(12) United States Patent
Sullenger et al.

(10) Patent No.: US 10,808,335 B2
(45) Date of Patent: *Oct. 20, 2020

(54) ELECTROSPUN CATIONIC NANOFIBERS AND METHODS OF MAKING AND USING THE SAME

(71) Applicant: DUKE UNIVERSITY, Durham, NC (US)

(72) Inventors: Bruce A. Sullenger, Durham, NC (US); Hemraj A. Juwarker, Durham, NC (US); Kam W. Leong, Durham, NC (US); Jennifer Gamboa Jackman, Durham, NC (US)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/120,988

(22) Filed: Sep. 4, 2018

(65) Prior Publication Data

US 2019/0136416 A1 May 9, 2019

Related U.S. Application Data

(62) Division of application No. 15/304,416, filed as application No. PCT/US2015/026201 on Apr. 16, 2015, now Pat. No. 10,066,323.

(60) Provisional application No. 61/980,414, filed on Apr. 16, 2014.

(51) Int. Cl.

| | | |
|---|---|---|
| *D01F 6/22* | (2006.01) | |
| *B29C 48/88* | (2019.01) | |
| *D01D 5/00* | (2006.01) | |
| *D01F 6/36* | (2006.01) | |
| *D01F 6/42* | (2006.01) | |
| *D06M 14/10* | (2006.01) | |
| *A61L 15/46* | (2006.01) | |
| *D06M 15/285* | (2006.01) | |
| *D06M 15/00* | (2006.01) | |
| *A61L 15/24* | (2006.01) | |
| *A61L 15/44* | (2006.01) | |
| *A61L 27/16* | (2006.01) | |
| *A61L 27/54* | (2006.01) | |
| *D06M 15/59* | (2006.01) | |
| *D06M 15/61* | (2006.01) | |
| *D06M 101/20* | (2006.01) | |
| *D06M 101/26* | (2006.01) | |

(52) U.S. Cl.
CPC ............ *D01F 6/22* (2013.01); *A61L 15/24* (2013.01); *A61L 15/44* (2013.01); *A61L 15/46* (2013.01); *A61L 27/16* (2013.01); *A61L 27/54* (2013.01); *B29C 48/88* (2019.02); *D01D 5/003* (2013.01); *D01F 6/36* (2013.01); *D01F 6/42* (2013.01); *D06M 14/10* (2013.01); *D06M 15/00* (2013.01); *D06M 15/285* (2013.01); *D06M 15/59* (2013.01); *D06M 15/61* (2013.01); *A61L 2300/404* (2013.01); *A61L 2300/41* (2013.01); *A61L 2400/12* (2013.01); *D06M 2101/20* (2013.01); *D06M 2101/26* (2013.01); *D06M 2400/01* (2013.01); *D10B 2509/022* (2013.01)

(58) Field of Classification Search
CPC ........................................................ D01F 6/22
USPC ........................................................ 514/54
See application file for complete search history.

(56) References Cited

U.S. PATENT DOCUMENTS

| | | |
|---|---|---|
| 7,300,922 B2 | 11/2007 | Sullenger et al. |
| 7,304,041 B2 | 12/2007 | Rusconi |
| 7,611,835 B2 | 11/2009 | wKim et al. |
| RE43,612 E | 8/2012 | Anderson et al. |
| 10,066,323 B2 * | 9/2018 | Sullenger ............... D01D 5/003 |
| 2003/0083294 A1 | 5/2003 | Sullenger et al. |
| 2003/0143217 A1 | 7/2003 | Baird et al. |
| 2003/0180250 A1 | 9/2003 | Chauhan et al. |
| 2006/0040881 A1 | 2/2006 | Rusconi |
| 2008/0199485 A1 | 8/2008 | Kundig et al. |
| 2008/0267903 A1 | 10/2008 | Uchegbu et al. |
| 2009/0048193 A1 | 2/2009 | Rusconi et al. |
| 2009/0082250 A1 | 3/2009 | Hart et al. |
| 2009/0208501 A1 | 8/2009 | Visintin et al. |
| 2009/0298710 A1 | 12/2009 | Farokhzad et al. |
| 2010/0210746 A1 | 8/2010 | Gustafson et al. |
| 2010/0249217 A1 | 9/2010 | Sullenger et al. |
| 2010/0285081 A1 | 11/2010 | Chen et al. |

(Continued)

FOREIGN PATENT DOCUMENTS

| | | |
|---|---|---|
| WO | WO 2002/019822 | 3/2002 |
| WO | WO 2003/002592 | 1/2003 |

(Continued)

OTHER PUBLICATIONS

Bompiani et al. "Probing the Coagulation Pathway with Aptamers Identifies Combinations that Synergistically Inhibit Blood Clot Formation" (2014) Chemistry & Biology 21: 935-944.

(Continued)

*Primary Examiner* — Nizal S Chandrakumar
(74) *Attorney, Agent, or Firm* — Quarles & Brady LLP

(57) ABSTRACT

Methods of making polycationic nanofibers by grafting cationic polymers onto electrospun neutral nanofibers and polycationic nanofibers produced by the methods are provided herein. In addition, methods of using the polycationic nanofibers to reduce inflammation, to adsorb anionic compounds such as heparin or nucleic acids, to inhibit the growth of microbes or inhibit the formation of a biofilm are also provided. The polycationic nanofibers may be in a mesh and may be included in a medical device, wound dressing, bandage, or as part of a graft.

15 Claims, 16 Drawing Sheets

(56) References Cited

U.S. PATENT DOCUMENTS

| 2011/0118187 | A1 | 5/2011 | Sullenger et al. |
| 2012/0128782 | A1 | 5/2012 | Green et al. |
| 2012/0183564 | A1 | 7/2012 | Sullenger |
| 2013/0266664 | A1 | 10/2013 | Yang et al. |

FOREIGN PATENT DOCUMENTS

| WO | WO 2006/040579 | 4/2006 |
| WO | WO 2008/000517 | 1/2008 |
| WO | WO 2008/063157 | 5/2008 |
| WO | WO 2008/121354 | 10/2008 |
| WO | WO 2010/020008 | 2/2010 |
| WO | WO 2011/034583 | 3/2011 |
| WO | WO 2013/040522 | 3/2013 |

OTHER PUBLICATIONS

Chase, et al., "Single-stranded DNA binding proteins required for DNA replication," (1986) Ann. Rev. Biochem. 55:103-136.
Fuchs, T. et al., "Extracellular DNA traps promote thrombosis," (2010) PNAS, 107(36):15880-15885.
Holl, et al., "Nucleic acid scavenging polymers inhibit extracellular DNA-mediated innate immune activation without inhibiting antiviral responses," (2013) Plos One, 8(7):1-10.
Holl et al., "The nucleic acid scavenger polyamidoamine third-generation dendrimer inhibits fibroblast activation and granulation tissue contraction" (2014) Plast Reconstr Surg 134: 420e-33e.
Joachimi, A. et al., "A new anticoagulant-antidote pair: Control of thrombin activity by aptamers and porphyrins," (2007) Journal of the American Chemical Society 129(11):3036-3037.
Kannemeier, C. et al, "Extracellular RNA constitutes a natural procoagulant cofactor in blood coagulation," (2007) PNAS, 104(15):6388-6393.
Kawai, T and Akira, S, "The role of pattern-recognition receptors in innate immunity: update on Toll-like receptors," (2010) Nat Immunol 11(5):373-84.
Lee et al., "Nucleic acid-binding polymers as anti-inflammatory agents," (2011) Proc. Natl. Acd. Sci. 108(34):14055-60.
Lee et al., "Electrospun nanofibers as versatile interfaces for efficient gene delivery," (2014) Journal of Biological Engineering 8(30):1-19.
Lichner, Z. et al., "Double-stranded RNA-binding proteins could suppress RNA interference-mediated antiviral defences," (2003) J. Gen. Virol. 84(4):975-980.
Merai, Z. et al., "Double-stranded RNA binding may be a general plant RNA viral strategy to suppress RNA silencing," (2006) J. Virol. 80(12):5747-5756.
Oney, S. et al., "Development of universal antidotes to control aptamer activity," (2009) Nature Medicine, 15(10):1224-1229.
Que-Gewirth, N.S. et al., "Gene therapy progress and prospects: RNA aptamers," (2007) Gene Therapy 14(4):283-291.
Rusconi, C.P. et al., "RNA aptamers as reversible antagonists of coagulation factor IXa," (2002) Nature 419(5):90-94.
Rusconi, C.P. et al., "Antidote-mediated control of an anticoagulant aptamer in vivo," (2004) Nature Biotechnology 22(11):1423-1428.

White, R. R. et al., "Developing aptamers into therapeutics," (2000) J. Clin. Investigation 106(8):929-934.
Yu, P., "Nucleic Acid recognizing Toll-like receptors as therapeutic targets: a focus on autoimmunity and cancer", Journal of Receptor, (2009) Ligand and Channel Research 2:19-28.
International Search Report and Written Opinion for PCT/US2008/004119 dated Jun. 26, 2008.
International Search Report and Written Opinion for PCT/US2010/002516 dated Jun. 10, 2011.
International Search Report and Written Opinion for PCT/US2015/026201 dated Jul. 8, 2015.
Supplemental European Search Report dated Jun. 27, 2013 issued in connection with EP 10 81 7556.
Office Action dated Nov. 4, 2014 for U.S. Appl. No. 13/496,313.
Office Action dated Jun. 3, 2015 for U.S. Appl. No. 13/496,313.
Office Action dated Feb. 24, 2011 for U.S. Appl. No. 12/588,016.
Office Action dated Sep. 19, 2011 for U.S. Appl. No. 12/588,016.
Office Action dated Jul. 10, 2013 for U.S. Appl. No. 12/588,016.
Office Action dated Jul. 3, 2014 for U.S. Appl. No. 12/588,016.
Office Action dated Dec. 3, 2014 for U.S. Appl. No. 12/588,016.
Office Action dated Jun. 8, 2015 for U.S. Appl. No. 12/588,016.
Office Action dated Oct. 30, 2015 for U.S. Appl. No. 12/588,016.
Lin et al., "Mechanism of bactericidal and fungicidal activities of textiles covalently modified with alkylated polyethylenimine," (2003) Biotechnol Bioeng 83(2):168-72.
Wan et al., "A chemistry/physics pathway with nanofibrous scaffolds for gene delivery," (2010) Phys Chem Chem Phys 12(39):12379-89.
Pisetsky, D.S. et al., "Nucleic acid-binding polymers as anti-inflammatory agents: reducing the danger of nuclear attack" (2012) Expert Rev Clin Immunol. 8(1):1-3.
Duan, X. et al., "Amphiphilic graft copolymer based on poly(styrene-co-maleic anhydride) with low molecular weight polyethylenimine for efficient gene delivery" (2012) Intl J. Nanomedicine 7:4961-4972.
Qui et al., (2005) Polymer Preprints 46(2), 1244-1245.
Xia et al., "Mimic of Protein: A Highly pH-Sensitive and Thermoresponsive Polyampholyte," (2011) Macromol. Chem. Phys 212, 2268-2274.
Chao, C.H. et al., "Cytotoxic and anti-inflammatory cembranoids from the soft coral *Lobophytum crassum*" (2008) J. Nat. Prod. 71(11):1819-1824.
Taher, M. et al., "Cytotoxic, anti-inflammatory and adipogenic effects of inophyllum d, calanone, isocordato-oblongic acid, and morelloflavone on cell lines," (2016) Natural Product Sciences 22(2):122-128.
Office Action dated Sep. 11, 2017 for U.S. Appl. No. 15/304,416 (15 pages).
Office Action dated Jan. 9, 2018 for U.S. Appl. No. 15/304,416 (8 pages).
Advisory Action dated Mar. 15, 2018 for U.S. Appl. No. 15/304,416 (4 pages).
Restriction Requirement dated Apr. 6, 2017 for U.S. Appl. No. 15/304,416 (9 pages).
Examiner Initiated Interview Summary dated Aug. 21, 2017 for U.S. Appl. No. 15/304,416 (4 pages).
Examiner Initiated Interview Summary dated Mar. 15, 2018 for U.S. Appl. No. 15/304,416 (3 pages).

* cited by examiner

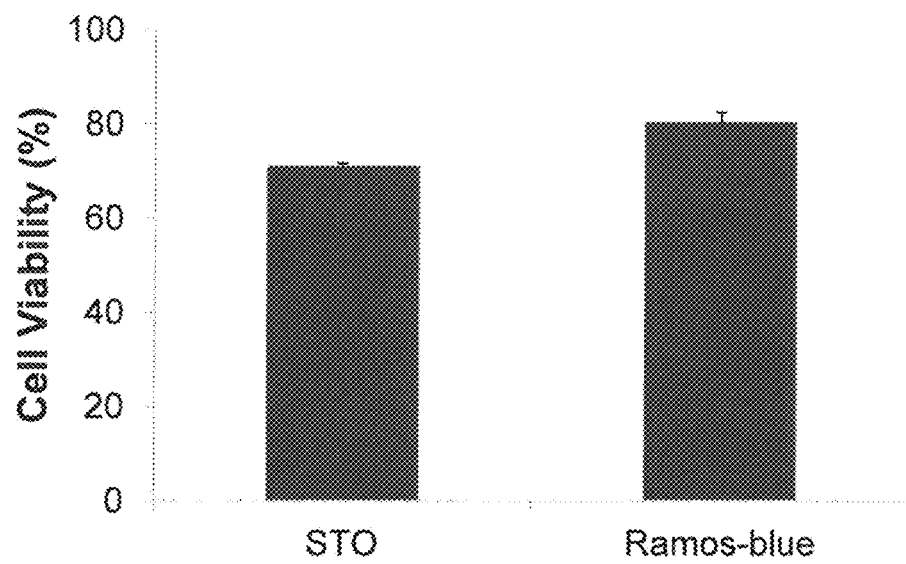
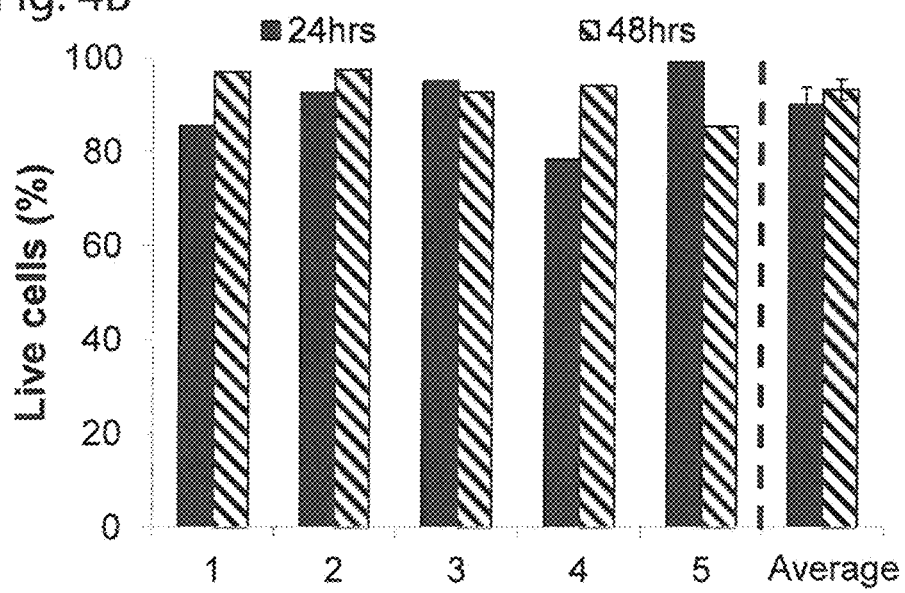

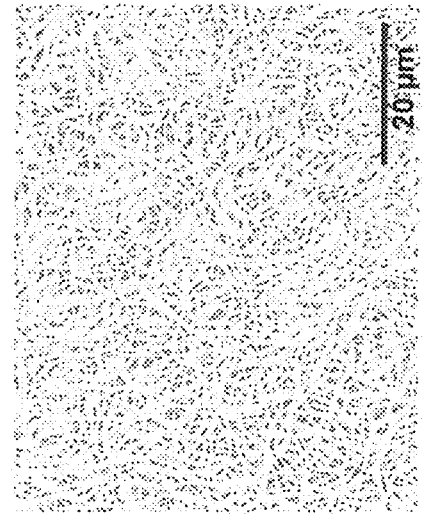
Fig. 5A
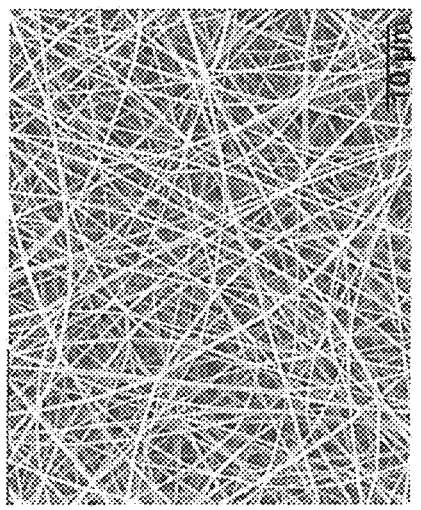
Fig. 5B
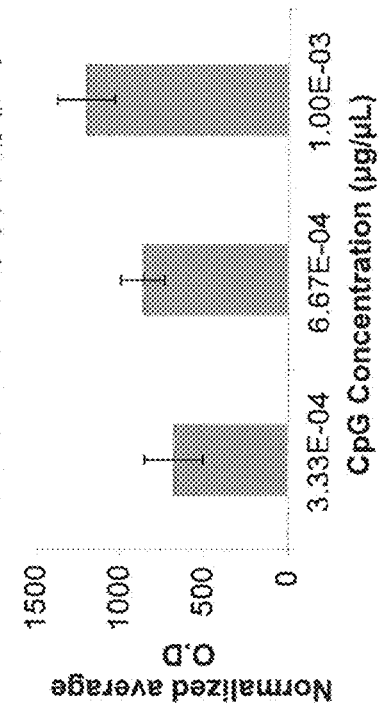
Fig. 5C
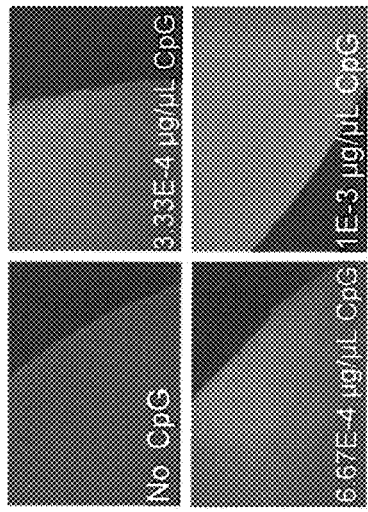
Fig. 5D
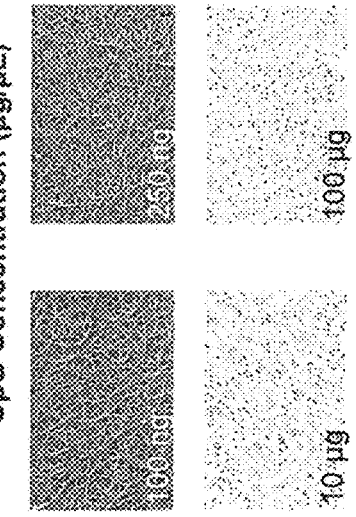
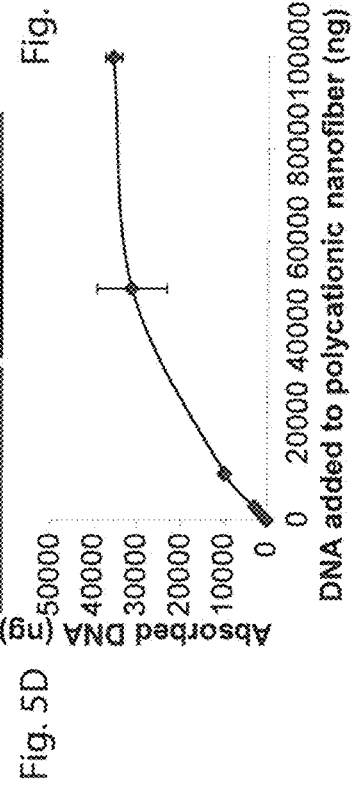
Fig. 5E

ELECTROSPUN CATIONIC NANOFIBERS AND METHODS OF MAKING AND USING THE SAME

CROSS-REFERENCE TO RELATED APPLICATIONS

This patent application is a divisional of U.S. Utility patent application Ser. No. 15/304,416, filed Oct. 14, 2016, which is a national stage filing under 35 U.S.C. 371 of International Application No. PCT/US2015/026201, filed Apr. 16, 2015, which claims the benefit of priority of U.S. Provisional Patent Application No. 61/980,414, filed Apr. 16, 2014, all of which are incorporated herein by reference in their entireties.

STATEMENT REGARDING FEDERALLY SPONSORED RESEARCH

This invention was made with United States government support awarded by the National Institutes of Health grant number R56AI093900. The United States has certain rights in this invention.

BACKGROUND

Nucleic acids are released from dead and dying cells. These extracellular nucleic acids (RNAs and DNAs) can be taken up by immune cells that release inflammatory signals and can activate multiple Pattern Recognition Receptors (PRR) such as the Toll-Like Receptors (TLRs 3, 7, 8 and 9 in particular), which are localized in endosomes (Kawai and Akira, Nat. Immunol. 11(5):373-84 (2010)). The inappropriate activation of these TLRs can elicit a variety of inflammatory and autoimmune diseases, for example, systemic lupus erythematosus, rheumatoid arthritis, multiple sclerosis, diabetes and chronic wounds.

It has been previously reported that certain nucleic acid-binding molecules (e.g., PAMAM-G3, CDP, HDMBr, protamine, polyethylenimine) can inhibit activation of nucleic acid-sensing PRRs, irrespective of whether they recognize ssRNA, dsRNA or hypomethylated DNA (Lee et al, Proc. Natl. Acad. Sci. USA 108(34):14055-60 (2011)). Means of using these nucleic acid binding molecules to inhibit aberrant inflammation without compromising immune responsiveness systemically are needed in the art.

In addition, biofilms often form in wound sites causing persistent inflammation and infection. These biofilms reduce the ability of the wound to heal. Means of reducing the ability of microorganisms to form biofilms are also needed. Methods of inhibiting the ability of microorganisms to grow in wound sites or in or on medical devices are also needed.

SUMMARY

Compositions comprising polycationic nanofibers, methods of making and methods of using the same are provided herein.

Polycationic nanofibers may be made by electrospinning a neutral polymer with an acyl, anhydride or carboxyl group to form nanofibers with diameters of less than 2 μm and grafting the a cationic polymer, such as an amine containing polymer, onto the nanofibers to allow covalent bonds to form via an amide covalent linkage to generate polycationic nanofibers.

Compositions comprising the polycationic nanofibers are also provided. These polycationic nanofibers may be incorporated into medical devices, used in filtration units, cut into pieces for direct addition to a solution or use in a medical device or used as a dressing for a wound or at a site of inflammation or infection.

The polycationic nanofibers may be used by adding the nanofibers to a solution or contacting the nanofibers with a solution to scavenge or adsorb anionic compounds or microbes in the solution. The interaction with the nanofibers can prevent microbes from forming biofilms. The anionic compounds may be nucleic acid mediators of inflammation.

In another alternative, the polycationic nanofibers may be administered to a subject in need of treatment for inflammation or reversing the effects of an anti-coagulant such as heparin. The polycationic nanofibers adsorb anionic inflammatory mediators thus reducing inflammation. The nanofibers may also inhibit the growth of microbes and/or inhibit the formation of biofilms.

In yet another aspect, the polycationic nanofibers are useful in medicaments for treating inflammation or infectious wound healing.

BRIEF DESCRIPTION OF THE DRAWINGS

FIG. 4A and FIG. 4B are a set of graphs showing the affect of the nanofibers on cells. FIG. 4A is a graph showing the percentage cell viability after addition of the indicated nanofibers for 4 hours to adherent cells (fibroblasts; STO cells) and non-adherent (B lymphoma cells; Ramos-blue). FIG. 4B shows that the nanofibers do not inhibit proliferation by showing an increase in the percentage of live NHDF cells (normal human dermal fibroblasts) from 24 to 48 hours.

FIGS. 5A-5E provide a set of data showing the nanofibers and the ability of the nanofibers to bind CpG and DNA. FIG. 5A is an SEM image of neutral PSMA nanofibers. FIG. 5B is an SEM image of 1.8 kDa modified PSMA nanofibers. FIG. 5C (left) is a set of fluorescent microscope images of polycationic nanofibers after 4 hrs interaction with varying concentrations of AlexaFluor488-CpG. The right side of FIG. 5C shows a graph quantifying the average fluorescence after interaction with AlexaFluor488-CpG normalized to auto-fluorescence of polycationic nanofiber alone, with the x axis indicating the initial amount of AlexaFluor488-CpG added. FIG. 5D is a graph showing salmon sperm DNA absorption onto the polycationic nanofiber. FIG. 5E is a set of SEM images of polycationic nanofibers following interaction with salmon sperm DNA.

FIG. 14A is an SEM showing polycationic nanofibers which were not exposed to bacteria. FIG. 14B is an SEM showing *Pseudomonas aeruginosa* bacteria and biofilm infiltrating the polycationic nanofibers. FIG. 14C and FIG. 14D show SEM at two different magnifications of the *Pseudomonas aeruginosa* bacteria biofilm growth on the surface of the polycationic nanofibers.

FIG. 16A and FIG. 16B show wild-type *Staphylococcus aureus* after 48 hours incubation at 37° C. with the polycationic nanofibers.

FIG. 16C and FIG. 16D show coagulase negative *Staphylococcus aureus* on polycationic nanofibers after 48 hrs incubation at 37° C.

DETAILED DESCRIPTION

Figure 1:
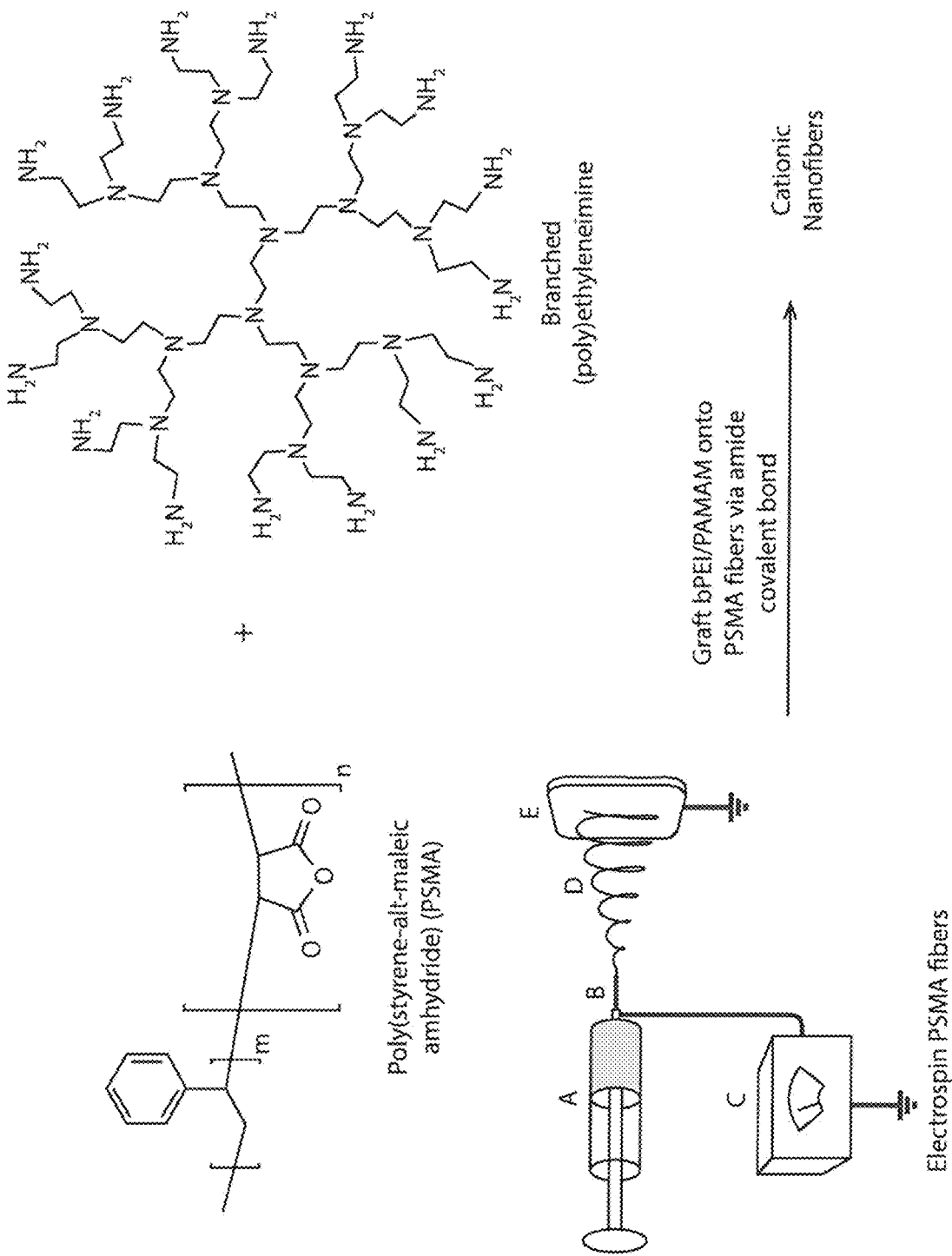
FIG. 1 is a schematic showing the polymers used and the method of making the polycationic nanofibers provided in the Examples.

The present invention results, at least in part, from studies designed to develop non-toxic, nucleic acid-binding polymers that form stable polyplexes with extracellular, pro-inflammatory nucleic acids and prevent cellular uptake, thereby inhibiting PRR activation, in particular TLR3, 7, 8, and 9 or RIG-I activation and reducing cytokine production and NF-κB induction in response to nucleic acid agonists of these receptors or administration of another anionic compound such as heparin. Nucleic acid agonists include any nucleic acid or nucleic acid complex capable of activating a PRR and inducing a cell to produce cytokines such as IL-6. Nucleic acid agonists include dsRNA, ssRNA, un- or hypomethylated DNA or ssDNA, and any of the aforementioned complexed with proteins.

As described herein, an electrospun scaffold comprising polycationic nanofibers can be used to scavenge anionic compounds. These polycationic nanofibers are being developed as novel ex vivo or topical in vivo scavengers of a) pro-inflammatory, immunostimulatory anionic molecules (e.g. DNA, RNA, LPS, heparan sulfate) b) anionic anticoagulant polymers (e.g. heparin, enoxaparin, RNA aptamers) and c) microorganisms, in particular microorganisms capable of forming biofilms. The immediate translation of these polycationic nanofibers has been in the development of a novel dressing for chronic wound healing. Additionally, we are pursuing the translation of these polycationic nanofibers into a novel membrane to be used in an ex vivo extracorporeal circuit for hemofiltration or for use in other ex vivo or in vitro applications to remove or deplete anionic compounds from a solution. Use of the polycationic nanofibers described herein in medical devices, at sites of inflammation such as sites of chemotherapeutic treatment or other treatment likely to induce cell death or inflammation, or at wound sites in vivo is also contemplated.

Our method of polycationic nanofiber formation is superior in its ease of formation and replicability. The resulting polycationic nanofibers are stable over time at room temperature and easy to manipulate or form into shapes for use in a variety of applications. Our technology consists of a modular approach to generate cationic nanofibers from any amine-containing polycationic polymer; this allows for tunability in the size and charge of the attached polycation thus broadening the scavenging capabilities of the fibers. Briefly, a neutral polymer with an acyl, anhydride or carboxyl reactive group is electrospun using methods known to those of skill in the art into nanofibers less than 2 μm in diameter. The polycationic nanofibers are between 0.1 and 2 μm, 0.2 and 1.5 μm or 0.3 and 1.0 μm in diameter. In the Examples, polystyrene maleic anhydride (PSMA) was used as the neutral polymer and electrospun into nanofibers. In the Examples, the neutral polymer was dissolved in a solution such as acetone, dimethylformamide (DMF), tetrahydrofuran (THF) or combinations thereof at a concentration between 40% and 200% (w/v). In the Examples a 1:1:1 solution of acetone, DMF and THF was used, but the combination of solvents can be varied. Suitably 45, 50, 55, 60, 65% or higher concentrations of the neutral polymer are used. Suitably less than 200%, 190, 180, 175, 170, 160, 150, 140, 130, 120, 110% of the neutral polymer are used for electrospinning. Electrospinning may be completed using between 10 and 22 volts and between 50 and 200 revolutions per minute. Suitably the voltage used for electrospinning is between 13 and 17 volts, the voltage may be 10, 11, 12, 13, 14, 15, 16, 17, 18, 19 or 20 volts. The revolutions per minute used in the Examples was 130, but 100-150 is suitable. The concentration of the neutral polymer used, the voltage, the combination of solvents used and the rate of flow and the revolutions per minute will determine the characteristics such as the diameter of the resulting nanofibers.

The nanofibers were then grafted with a cationic polymer with a free amine group such as polyethyleneimine (PEI), branched PEI (bPEI), polyamidoamine (PAMAM), in particular PAMAM generations 0-4 or other dendrimers or positively charged copolymers such as those identified in International Patent Publication No. 2014/169043 and United States Patent Publication No. 2010/0184822, both of which are incorporated herein by reference in their entireties. Other cationic polymers useful in the methods include, but are not limited to N,N'-cystaminebisacrylamide and N,N'-hexamethalyne bisacrylamide backbone components with histamine and 3-(dimethylamino)-1-propylamine linkers. The grafting may be completed by soaking or incubating the neutral nanofibers with the cationic polymer. The cationic polymer may be present in a solution at 0.009M to 1M and the cationic polymers and neutral nanofibers may be co-incubated for 12 hours or more. In the Examples the nanofibers and cationic polymer were co-incubated for 24-48 hours in a 0.1M solution of bPEI or a 0.01M PAMAM. The polycationic nanofibers may be made into any form such as a mesh, filter or other form and may be used in medical devices, filters, bandages or wound dressings as well as in other formulations available to those of skill in the art. The nanofibers can be cut or formed into any suitable shape. Punched out discs were used in some of the Examples.

We hypothesized that the incorporation of cationic polymers onto insoluble nanofibers would enable the scavenging of pro-inflammatory species directly from blood, wounds or other solutions, reducing cytotoxicity related to unwanted internalization of the polymers. Herein, we report preliminary, in vitro data to support that electrospun nanofibers grafted with cationic polymers can absorb agonists of TLR 3, 7, 8, 9 directly from serum or medium and prevent the production of NF-κB, an immune system activating transcription factor while also demonstrating reduced cytotoxicity. We also demonstrate that the polycationic nanofibers can reduce the formation of biofilms and prevent or slow the proliferation of at least some microbes such as *Staphylococcus*.

Thus methods of using the composition containing the polycationic nanofibers provided herein are provided. The methods include adding the polycationic nanofibers to a solution containing or suspected of containing an anionic compound capable of binding and activating a PRR. The polycationic nanofibers may be contacted with a solution or applied to a site of inflammation suspected of containing an anion or anionic compound or a microorganism. The polycationic nanofibers described herein may be contacted with a solution, cells or tissues directly or indirectly in vivo, in vitro, or ex vivo. Contacting encompasses administration to a cell, tissue, mammal, patient, or human. Further, contacting includes adding the polycationic nanofibers to a cell culture to a wound site or site of inflammation or to a solution. Other suitable methods may include introducing or administering the polycationic nanofibers to a solution, cell, tissue, mammal, or patient using appropriate procedures and routes of administration as defined below.

In some embodiments the polycationic nanofibers are administered to a subject. Administration includes topical, subcutaneous, transcutaneous or any other means of bringing the polycationic nanofibers in contact with the subject and the site of inflammation, infection or other site at which anionic compounds need to be adsorbed. The polycationic nanofibers described herein may be administered in an amount and way such that the polycationic nanofibers are in an effective amount to treat a condition, such as inflammation, infection or reversal of the effects of an anionic compound. An effective amount or a therapeutically effective amount as used herein means the amount of the nanofibers that, when administered to a subject for treating a state, disorder or condition is sufficient to effect a treatment. The therapeutically effective amount will vary depending on the compound, formulation or composition, the disease and its severity and the age, weight, physical condition and responsiveness of the subject to be treated. Treating a subject as used herein refers to any type of treatment that imparts a benefit to a subject afflicted with a disease or a condition or at risk of developing the disease or condition, including improvement in the condition of the subject (e.g., in one or more symptoms), delay in the progression of the disease or condition, delay the onset of symptoms or slow the progression of symptoms, etc.

Without being limited by theory the inventors believe that the anionic compounds are adsorbed onto the polycationic nanofibers and not allowed to interact with the PRR on the cells and this prevents inflammation. The anionic compounds include nucleic acids, such as DNA or RNA, or heparin or heparin analogs, in particular low molecular weight heparins, enoxaparin or other anionic compounds. The solution includes a wound site, blood, serum, synovial fluid, saliva, water, culture media, or other biological fluids. The methods also include administering the polycationic nanofibers to a subject in an amount effective to adsorb anionic compounds in the subject.

Electrospun PSMA fibers modified with bPEI can inhibit the activation of Toll-like receptors (TLRs) by pro-inflammatory nucleic acids. These polycationic nanofibers show specificity for negatively charged agonists and demonstrate promise for developing novel dressings and treatments for inflammation in chronic wound healing in which a sustained immune response prevents completion of wound healing, thus leaving wounds open and exposed to further infection. A cationic fiber bandage has potential to eliminate immune agonists and promote wound healing, for example in chronic wounds. We are currently investigating the utility of these nanofibers in animal models for chronic wound healing and control of inflammation and microbial growth.

The polycationic nanofibers suitably have low or no cytotoxicity. As shown in the Examples, the polycationic nanofibers have demonstrated little or no cytotoxicity in three different cell lines: STO, RAMOS Blue, and human derived endothelial cells. The polycationic nanofibers provided herein can be exposed to cells or tissues as shown in the examples because the nanofibers are not cytotoxic or have low cytotoxicity when incubated with cells as compared to the viability of untreated cells. Low cytotoxicity indicates that cellular viability in cells treated with the polycationic nanofibers is reduced by less than 5%, 10%, 15%, 20%, 25%, 30%, 35%, 40%, 45% or 50% as compared to untreated control cells.

Administration or co-incubation of the polycationic nanofibers provided herein with a solution or at a site containing the nucleic acid agonists was required to inhibit PRR activation by a nucleic acid agonist. Co-incubation with the cells was not required and the polycationic nanofibers were used to scavenge the nucleic acids from a solution prior to addition to cells. The polycationic nanofibers provided herein either do not allow or inhibit cellular uptake of the nucleic acid agonists. Without being limited by theory, we hypothesize that the polycationic nanofibers provided herein work at least partially by adsorbing the anionic nucleic acids and thus inhibiting cellular uptake of the nucleic acid agonists of the PRRs. This inhibits interaction of the nucleic acid agonists with the receptors on the cells. The polycationic nanofibers may inhibit uptake of the nucleic acid or TLR agonists by 10%, 20%, 30%, 40%, 50% or even 60% or more as compared to control cells. The cellular response to the nucleic acids or TLR agonists is reduced by at least 10%, 20%, 30%, 40%, 50%, 60% or 70% when the polycationic nanofibers are present as compared to control cells treated with the nucleic acid agonists or with neutral nanofibers.

The present invention relates, in one embodiment, to methods of inhibiting nucleic acid-induced activation of PRRs, such as endosomal TLRs (e.g., TLR 9). The methods include adding polycationic nanofibers to cells (e.g., by adding the polycationic nanofibers to the extracellular space or media or pre-incubating the polycationic nanofibers with the media) or administering the polycationic nanofibers to a subject (e.g., a human in vivo or ex vivo) in need thereof. The polycationic nanofibers are capable of inhibiting the cellular response to nucleic acid induction of PRR (TLR) activation. The polycationic nanofibers are provided in an amount and under conditions such that inhibition of activation via the PRR is affected.

Advantageously, the polycationic nanofibers binds the nucleic acids in a manner that is independent of the nucleotide sequence, the chemistry (e.g., DNA or RNA, with or without base or sugar modifications) and/or the structure (e.g., double-stranded or single-stranded, complexed or uncomplexed with, for example, a protein) of the nucleic acids responsible for inducing nucleic acid receptor (TLR) activation. The present methods can be used to treat inflammatory and/or autoimmune responses resulting from inappropriate activation of nucleic acid receptors on or in cells. Administration or addition of the polycationic nanofibers inhibits activation of the nucleic acid receptor by 10%, 20%, 30%, 40%, 50%, 60%, 70%, 80% or more. Suitably inhibition is in a dose-dependent manor such that addition of small amounts of the polycationic nanofibers are not or only slightly capable of inhibiting receptor activation and addition of higher amounts of the polycationic nanofibers results in additional inhibition up to full inhibition of activation of the receptor by the nucleic acid or other TLR agonist. The percentage inhibition of the receptor may refer to the percentage inhibition or reduction in cytokine production (e.g. IL-6) or in activation of NF-κB in response to the agonist in combination with one or more of the polycationic nanofibers as compared to cells treated with the agonist alone or the agonist and an irrelevant polymer or nanofiber.

Advantageously, the binding affinity of a nucleic acid-binding polycationic nanofibers of the invention for a nucleic acid, expressed in terms of Kd, is in the pM to mM range, preferably, less than or equal to 50 nM; expressed in terms of binding constant (K), the binding affinity is advantageously equal to or greater than $10^5 M^{-1}$, preferably, $10^5 M^{-1}$ to $10^8 M^{-1}$, more preferably, equal to or greater than $10^6 M^{-1}$. Thus, the binding affinity of the sequence-independent nucleic acid-binding polycationic nanofibers can be, for example, about $1 \times 10^5 M^{-1}$, $5 \times 10^5 M^{-1}$, $1 \times 10^6 M^{-1}$, $5 \times 10^6 M^{-1}$, $1 \times 10^7 M^{-1}$, $5 \times 10^7 M^{-1}$; or about 10 µM, 100 µM, 1 nM, 10 nM, 100 nM, 1 µM, 10 µM, 100 µM. "K" and "Kd" can be determined by methods known in the art, including Isothermal calorimetry (ITC), Forster Resonance Energy Transfer (FRET), surface plasmon resonance or a real time binding assay such as Biacore.

Preferred nucleic acid-binding polycationic nanofibers of the invention simultaneously limit the activation of multiple nucleic acid binding PRRs (endosomal TLRs, e.g., TLR3, TLR7, TLR8 and TLR9 and possibly cytosolic nucleic acid sensors such as RIG-I) by binding to a wide array of different nucleic acids or other anionic compounds including but not limited to ssRNA, ssDNA, dsRNA and dsDNA and of which may be presented in a complex with protein such as viral proteins, histones, HMGB1 or RIG-I. Suitably the nucleic acid-binding polycationic nanofibers do not inhibit activation of non-nucleic acid binding TLRs such as TLR 2, TLR4, TLR5, or TLR6. For example, the polycationic nanofibers do not inhibit activation by LPS, lipoproteins, or flagellin. The polycationic nanofibers are minimally cytotoxic. The polycationic nanofibers also bind to many microbes and may affect microorganism proliferation or biofilm formation.

As indicated above, the present invention provides a method of controlling (inhibiting or preventing) autoimmune and/or inflammatory responses associated with activation of PRRs by nucleic acids or other anionic compounds or TLR agonists (e.g., endosomal TLRs, such as TLR9). Such responses play a role in the pathogenesis of diseases/disorders that are associated with presence in the circulation of the subject of free nucleic acids, either pathogen-derived (e.g., viral- or bacterial-derived) nucleic acids or nucleic acids released from dead or damaged host cells. Specific diseases/disorders that can be treated using nucleic acid-binding polycationic nanofibers of the invention include infectious diseases, cardiovascular disease, cancer, bacterial sepsis, multiple sclerosis, systemic lupus erythematosis, rheumatoid arthritis, inflammatory bowel disease, COPD, obesity, psoriasis, atherosclerosis, diabetes, wound healing, burns, infectious diseases, reperfusion injury, renal failure/dialysis, organ transplantation, neurodegenerative disease and traumatic brain injury. (See also International Patent Application No. PCT/US2010/002516, International Patent Publication No. WO2011/034583, filed Sep. 16, 2010.)

As shown in the Examples, the polycationic nanofibers are also able to inhibit the growth of microbes and formation of biofilms by microbes. The Examples demonstrate the ability of the polycationic nanofibers to reduce the formation of biofilms of *Pseudomonas aeruginosa* and prevent the proliferation of certain bacteria such as *Staphylococcus aureus* or coagulase negative *Staphylococcus aureus*. Thus the polycationic nanofibers are able to inhibit the growth of and biofilm production by both gram positive and gram negative bacteria and we expect the polycationic nanofibers will also inhibit biofilm production and growth of fungi, such as yeast.

Gram-positive bacteria capable of forming biofilms include, but are not limited to, *Bacillus* spp., *Corynebacterium* spp., *Listeria* spp. (i.e. *Listeria monocytogenes*), *Staphylococcus* spp. (i.e. *Staphylococcus aureus* and *Staphylococcus epidermis*), *Micrococcus* spp., and lactic acid bacteria (i.e. *Lactobacillus plantarum, Lactococcus lactis, Entercoccus* spp., *Streptococcus* spp. including *Streptococcus mutans* and *Streptococcus pneumoniae*). Gram-negative bacteria capable of forming biofilms include, but are not limited to, *Escherichia* spp. (i.e. *Escherichia coli*), *Klebsiella* spp. (i.e. *Klebsiella pneumonia*), *Pseudomonas* spp. (i.e. *Pseudomonas aeruginosa, Pseudomonas putida, Pseudomonas fluorescens*), *Proteus* spp., *Legionella* spp., *Rhizobium* spp. (i.e. *Rhizobium leguminosarum*), *Sinorhizo-*

*bium* spp. (i.e *Sinorhizobium meliloti*), and *Serratia* spp. Yeast capable of forming biofilms include, but are not limited to, *Candida* spp. (i.e. *Candida albicans*) and *Aspergillus* spp.

The polycationic nanofibers can also be used in combination with other treatments. The polycationic nanofibers may be used in conjunction with another therapeutic, such as a cancer therapeutic, known to result in a robust inflammatory response by releasing nucleic acids possibly from dead or dying cells. Such treatments may be treatments known to induce cell death or nucleic acid based inflammation. Administration of the polycationic nanofibers may limit inflammation associated with these treatments and alleviate side effects. In one embodiment, the polycationic nanofibers are administered to cells or a subject which previously received or were exposed to a nucleic acid-based pharmaceutical composition, such as an siRNA, a DNA vaccine or an aptamer based therapy. The polycationic nanofibers described herein may be useful to limit inflammatory side effects associated with administration of such therapeutics.

Another application of nucleic acid-binding polycationic nanofibers described herein is to counteract the effects of DNA, RNA or polyphosphate molecules that are released from cells and subsequently induce thrombosis (Kannemeier et al, Proc. Natl. Acad. Sci. 104:6388-6393 (2007); Fuchs et al, Proc. Natl. Acad. Sci. Published Online before Print Aug. 23, 2010). It has been observed that RNA and DNA molecules can activate the coagulation pathway as well as platelets and thereby engender blood clotting (Kannemeier et al, Proc. Natl. Acad. Sci. 104:6388-6393 (2007); Fuchs et al, Proc. Natl. Acad. Sci. Published Online before Print Aug. 23, 2010). Since nucleic acid-binding polycationic nanofibers described herein can bind RNA and DNA molecules and shield them from other potential binding partners, such agents can be employed to inhibit the ability of DNA and RNA molecules to bind and activate coagulation factors and platelets. In so doing, these RNA/DNA-binding polycationic nanofibers can be utilized to limit nucleic acid-induced pathological blood coagulation. Thus, nucleic acid-binding cationic polymers described herein represent novel entities for preventing the induction and progression of a variety of thrombotic disorders, including myocardial infarction, stroke and deep vein thrombosis.

The precise nature of the compositions of the invention will depend, at least in part, on the nature of the nucleic acid-binding polycationic nanofibers and the route of administration. It will be appreciated that the treatment methods of the present invention are useful in the fields of both human medicine and veterinary medicine. Thus, the patient (subject) to be treated can be a mammal, preferably a human. For veterinary purposes the subject can be, for example, a farm animal such as a cow, pig, horse, goat or sheep, or a companion animal such as a dog or a cat.

An effective amount or a therapeutically effective amount as used herein means the amount of a composition that, when administered to a subject for treating a state, disorder or condition is sufficient to effect a treatment. The therapeutically effective amount will vary depending on the composition, the disease and its severity and the age, weight, physical condition and responsiveness of the subject to be treated.

Suitably the polycationic nanofibers are also tested for the inability to block activation and cytokine production by cells in response to non-nucleic acid binding PRRs (TLRs) such as LPS activation of TLR4; Pam3CSK4 activation of TLR2; endogenous DAMP or heparan sulfate activation of TLR4. The polycationic nanofibers should also be tested for cytotoxicity to cells after incubation and for lack of toxicity when administered to subjects such as mice.

The present disclosure is not limited to the specific details of construction, arrangement of components, or method steps set forth herein. The compositions and methods disclosed herein are capable of being made, practiced, used, carried out and/or formed in various ways that will be apparent to one of skill in the art in light of the disclosure that follows. The phraseology and terminology used herein is for the purpose of description only and should not be regarded as limiting to the scope of the claims. Ordinal indicators, such as first, second, and third, as used in the description and the claims to refer to various structures or method steps, are not meant to be construed to indicate any specific structures or steps, or any particular order or configuration to such structures or steps. All methods described herein can be performed in any suitable order unless otherwise indicated herein or otherwise clearly contradicted by context. The use of any and all examples, or exemplary language (e.g., "such as") provided herein, is intended merely to facilitate the disclosure and does not imply any limitation on the scope of the disclosure unless otherwise claimed. No language in the specification, and no structures shown in the drawings, should be construed as indicating that any non-claimed element is essential to the practice of the disclosed subject matter. The use herein of the terms "including," "comprising," or "having," and variations thereof, is meant to encompass the elements listed thereafter and equivalents thereof, as well as additional elements. Embodiments recited as "including," "comprising," or "having" certain elements are also contemplated as "consisting essentially of" and "consisting of" those certain elements.

Recitation of ranges of values herein are merely intended to serve as a shorthand method of referring individually to each separate value falling within the range, unless otherwise indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure. Use of the word "about" to describe a particular recited amount or range of amounts is meant to indicate that values very near to the recited amount are included in that amount, such as values that could or naturally would be accounted for due to manufacturing tolerances, instrument and human error in forming measurements, and the like. All percentages referring to amounts are by weight unless indicated otherwise.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

The following examples are meant only to be illustrative and are not meant as limitations on the scope of the invention or of the appended claims.

EXAMPLES

Methods

Figure 2:
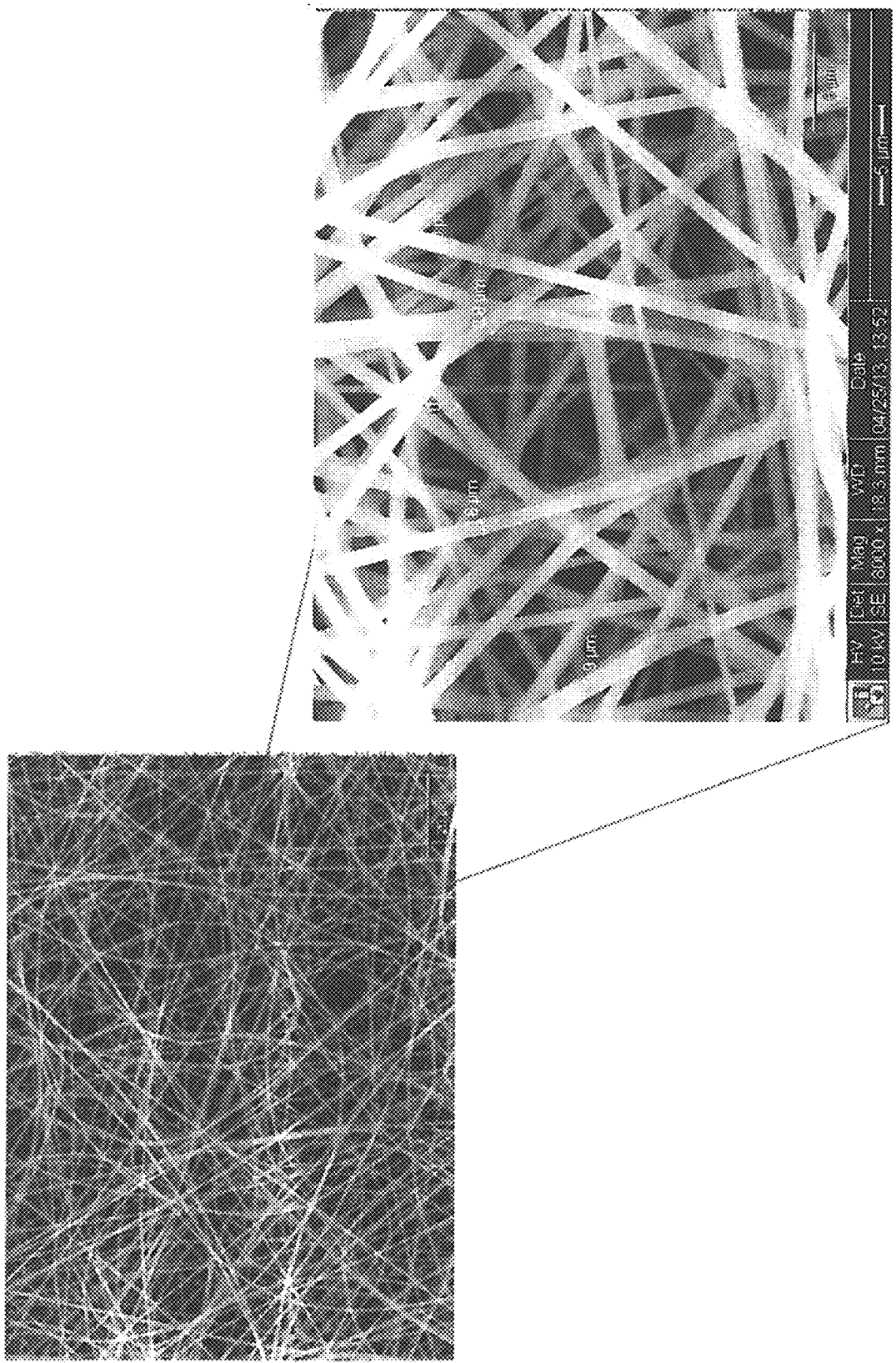
FIG. 2 is a set of photographs showing the scanning electron micrograph (SEM) images of the 100% polycationic nanofibers (100% poly-styrene maleic anhydride (PSMA) electrospun nanofibers with 1.8 kDa branched polyethyleneimine (bPEI) covalently attached at two different levels of magnification. The diameters of the fibers are shown in the photograph.
Figure 3:
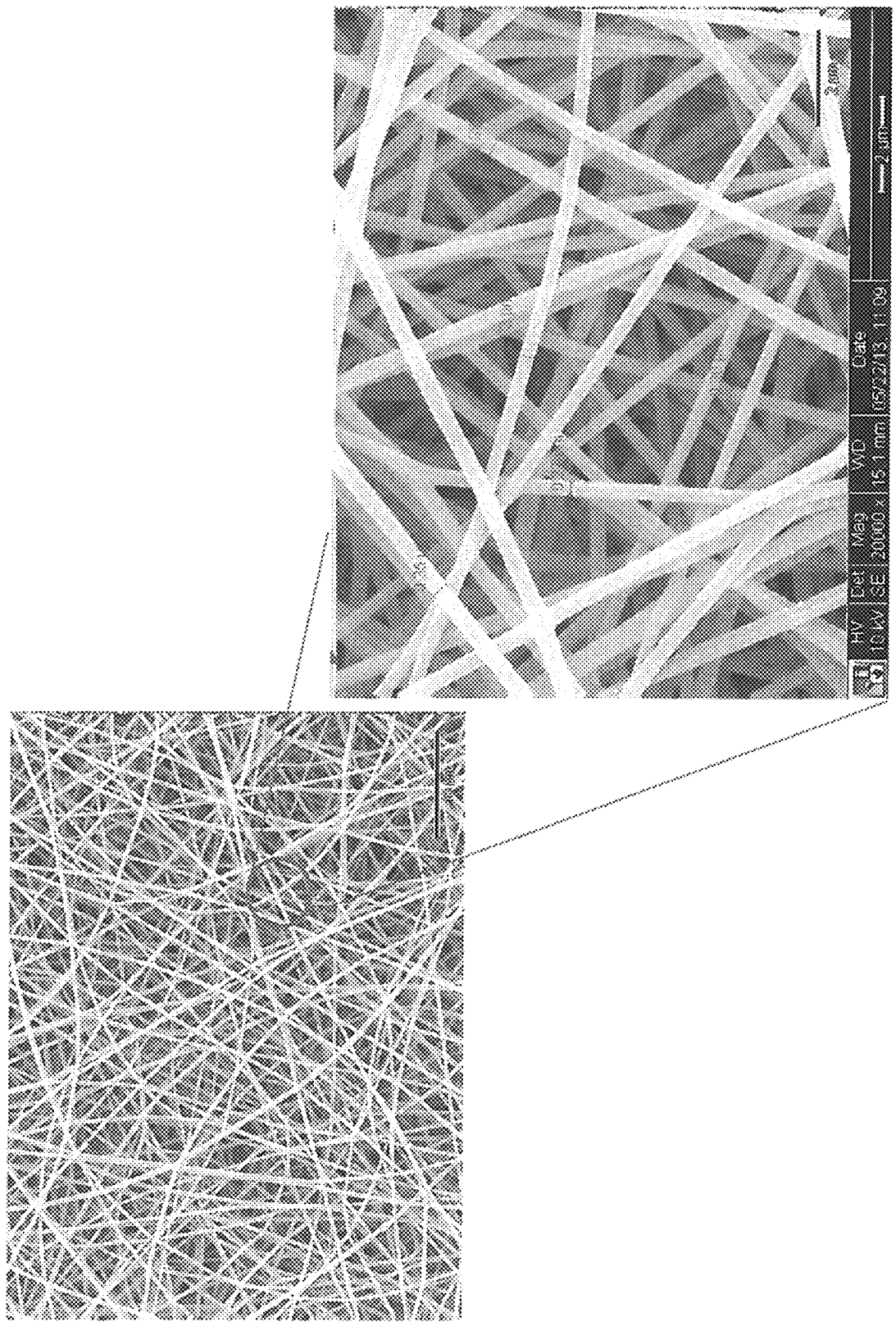
FIG. 3 is a set of photographs showing the scanning electron micrograph (SEM) images of the 60% polycationic nanofibers (60% PSMA nanofibers with covalently attached 1.8 kDa bPEI) at two different levels of magnification. The diameters of the fibers are shown in the photograph.

The method of making the polycationic nanofibers is shown schematically in FIG. 1. Briefly, unaligned nanofibers were fabricated by electrospinning a solution of 60% or 100% (w/v) Poly (styrene-co-maleic anhydride MW 350,000) in 1:1:1 (v/v) tetrahydrofuran, N,N dimethylformamide, and acetone at 15V. Nanofibers were collected on a fly-wheel 3.9 inches away from the solution source rotating at 130 revolutions per minute. Polycationic fibers were made by soaking the electrospun PSMA fibers in 0.1M 1.8 kDa branched poly(ethylenimine) (bPEI) in water or 0.01M Polyamidoamine dendrimer G3 (PAMAM-G3) in water for 48 hrs, then washed with DI water, and sterilized with ethanol for 20 min. Nanofibers were imaged and characterized using Scanning Electron Microscopy (SEM). FIGS. 2 and 3 show SEM photographs of the 100% PMSA and 60% PMSA cationic nanofibers, respectively. The 100% PMSA nanofibers had diameters of about 0.8-1 µm and the 60% PMSA cationic nanofibers were about 0.2-0.4 µm in diameter.

Cell viability studies were performed in mouse fibroblast cells (STO) and a B lymphocyte cell line (Ramos Blue™, Invivogen). Cell viability was determined by direct contact of the cells with the fibers. Cell proliferation studies were performed by plating strongly adherent cells, normal human dermal fibroblasts (NHDFs) directly onto fibers. Growth on polycationic nanofibers was encouraged by using a non-cell culture treated plate. Live/Dead staining and imaging was performed at 24 and 48 hrs followed by analysis using ImageJ. Cell-activation and specificity studies were performed with Ramos Blue™ cells by submerging fibers in serum free media with nucleic acid and non-nucleic acid based TLR agonists and subsequently treating the cells with the fiber-exposed medium. Resulting NF-κβ levels were measured using QUANTI-Blue™ (Invivogen) a secreted embryonic alkaline phosphate (SEAP) detection medium.

Nucleic acid absorption studies using labeled CpG and salmon sperm DNA were performed as follows. Varying concentrations of Alexa Fluor 488 labeled CpG were incubated with 3 mm fibers for 4 hrs at RT under constant shaking, protected from light. The fibers were washed 3 times with DI water, placed on a cover slip, mounted with SlowFade Diamond reagent, and fluorescent images are captured with an Upright AxioImager.A1 microscope powered by a Zeiss HBO100 power supply and lamp housing. To create the DNA absorption curve, varying amounts of salmon sperm DNA were added to 3 mm fibers for 4 hrs at RT under constant shaking. A total of 75 µL of 1×TE is used for the salmon sperm DNA, after 4 hrs 1-10 µL is removed from the fibers and the total salmon sperm DNA concentration is determined using PicoGreen.

Doxorubicin-induced cell death debris experiments were performed by plating RAW cells in a 96 well plate at 40 K cells per well and incubated for 18-24 hrs. Doxorubicin (DOX) was added at 3, 3.6, 6, or 9 µg/mL and incubated for 48 hrs. 100 µL of the supernatant from the DOX-treated cells was added to a 4 mm piece of PSMA-bPEI nanofiber. The fiber and supernatant were incubated for 30 min and the entire volume was added to 200 k RAMOS cells in 100 µL. 18-24 hrs later, 40 µL of the Ramos cells' supernatant was added to 160 µL of Quanti-blue and the absorbance was read at 650 nm at 3 and 5 hrs.

SEM images of biofilms on the polycationic nanofibers were taken after 48 hrs incubation of *Pseudomonas aeruginosa* or *Staphylococcus aureus*/Coagulase negative *Staphylococcus aureus* in LB broth at 37° C. with a starting concentration of $1\times10^5$ cells/mL. 100 µL of bacteria dispersion was incubated with a 4 mm diameter nanofiber followed by fixation and dehydration for SEM preparation. Biofilm mass of *Pseudomonas aeruginosa* was determined by incubating the bacterial dispersion or co-incubating the bacterial dispersion with polycationic nanofibers of 3 or 4 mm diameter for 48 hrs at 37° C., followed by 3 washes of PBS, a 15 minute room temperature incubation with 0.1% crystal violet, 3 more PBS washes, a 15 minute room temperature incubation with 30% acetone, and a final absorbance reading at 550 nm. The Colony Forming Units (CFUs) of *Staphylococcus aureus* were determined by measuring the absorbance at 600 nm of the bacterial dispersion following 48 hrs incubation at 37° C.

Results:

SEM shows that the fibers are randomly aligned and in the nanometer range 270-380 nm and 800-900 nm for 60% PSMA and 100% PSMA, respectively (See FIGS. 2 and 3). Cell viability studies with STO and Ramos blue cells show minimal toxicity of the fibers upon direct contact with the cells as shown in FIGS. 4A and 4B. The nanofibers were placed in the wells with the cells and allowed to incubate for 4 hours at 37° C. The fibers were removed from the wells and Cell Titer Glo (Promega, Madison, Wis.) was used to determine the cell viability. The minimal toxicity of the polycationic nanofibers, either 60%+bPEI and 100%+bPEI in FIG. 4A is presumably due to the increased basicity of the cell media from bPEI. FIG. 4B shows that the polycationic nanofibers do not affect the proliferation of NHDFs, showing that cells can still proliferate in the presence of the polycationic nanofiber.

Confirmation of successful preparation of polycationic nanofibers was demonstrated through the electrostatic interaction with negatively charged nucleic acids including CpG and salmon sperm DNA as shown in FIG. 5A-5E. Alexa Fluor labeled CpG demonstrated the interaction of nucleic acids with the polycationic nanofiber as shown in FIG. 5C. As expected, increasing amounts of CpG resulted in increased fluorescence as compared to background nanofiber fluorescence. The increased fluorescence of the polycationic nanofibers following soaking indicated that they were pulling the nucleic acids out of solution, therefore demonstrating functionality. Further absorption analysis using salmon sperm DNA as shown in FIG. 5D resulted in an absorption curve showing the absorption capacity of the polycationic nanofiber is ~30 µg/3 mm fiber disc. SEM images show that the initial modification of neutral nanofibers with bPEI results in swelling of the fibers and some "melting" of the fibers where they overlap and appear to connect; however, interaction with salmon sperm DNA does not change the morphology as shown in FIG. 5E.

Figure 6:
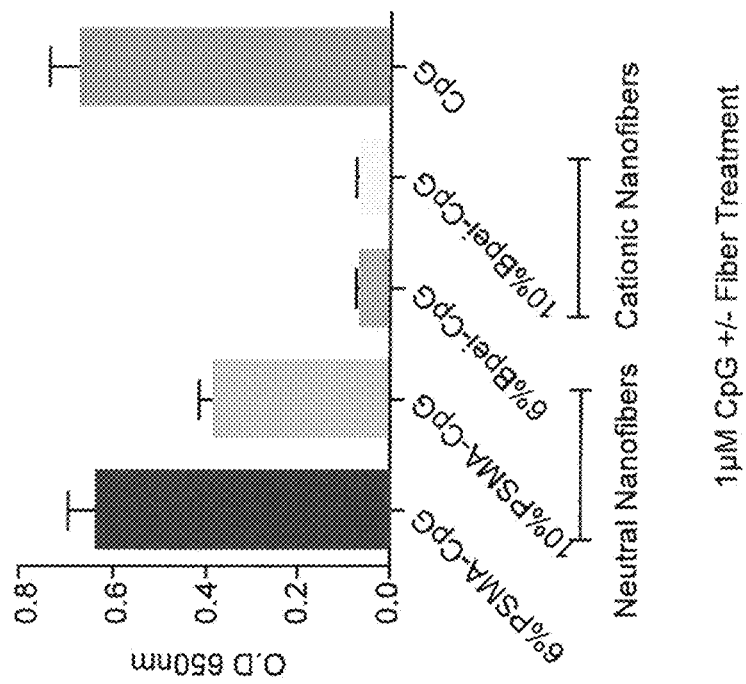
FIG. 6 is a graph showing that the polycationic nanofibers can block NF-κB expression caused by TLR activation by CpG whereas neutral nanofibers do not effectively block TLR activation by CpG therefore yielding high levels of NF-κB.
Figure 7:
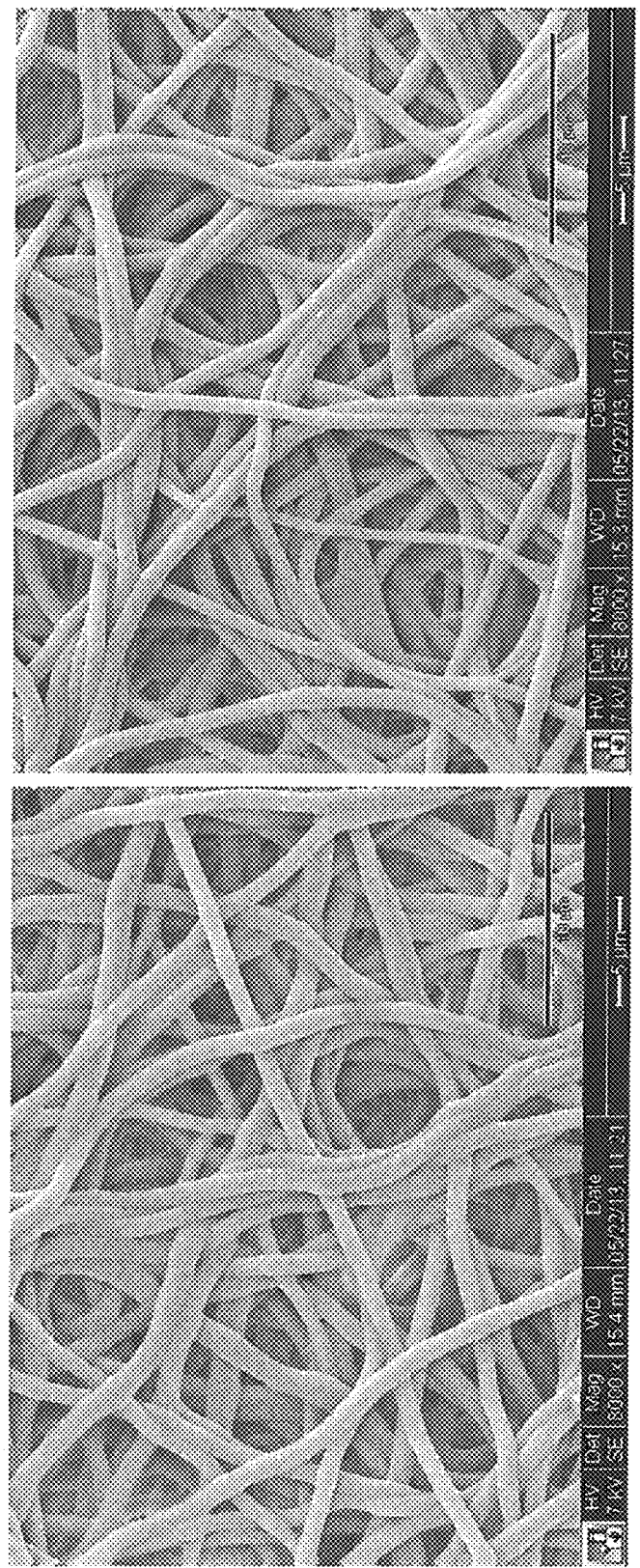
FIG. 7 is a set of SEM photographs showing the polycationic nanofibers made from 100% PSMA before (left) and after (right) interaction with CpG.

The ability of polycationic nanofibers to block expression of NF-kB was tested by incubating $2\times10^5$ B cells with the polycationic nanofibers or neutral nanofibers in the presence of CpG at 1 µM for 20 hours. Ramos B lymphocytes were obtained from Invivogen and express alkaline phosphatase from the NF-kB promoter such that alkaline phosphatase activity in the supernatant of these cells is indicative of NF-kB induction. The polycationic nanofibers effectively eliminated the immune stimulating response of NA based agonist CpG (TLR 9) while neutral nanofibers had little effect on the ability of CpG to stimulate NF-kB as shown in FIG. 6. Results show that unmodified PSMA fibers have no inhibitory effects, demonstrating that the fiber activity is not due to a physical or solvophobic interaction with the fibers. The cationic fibers (60%/100%+bPEI), reduced the Ramos Blue™ NF-κβ response to the baseline of unstimulated cells. FIG. 7 shows an SEM image of the 100% PSMA polycationic nanofibers after interaction with CpG. No change in structure is evident in the SEM.

Figure 8:
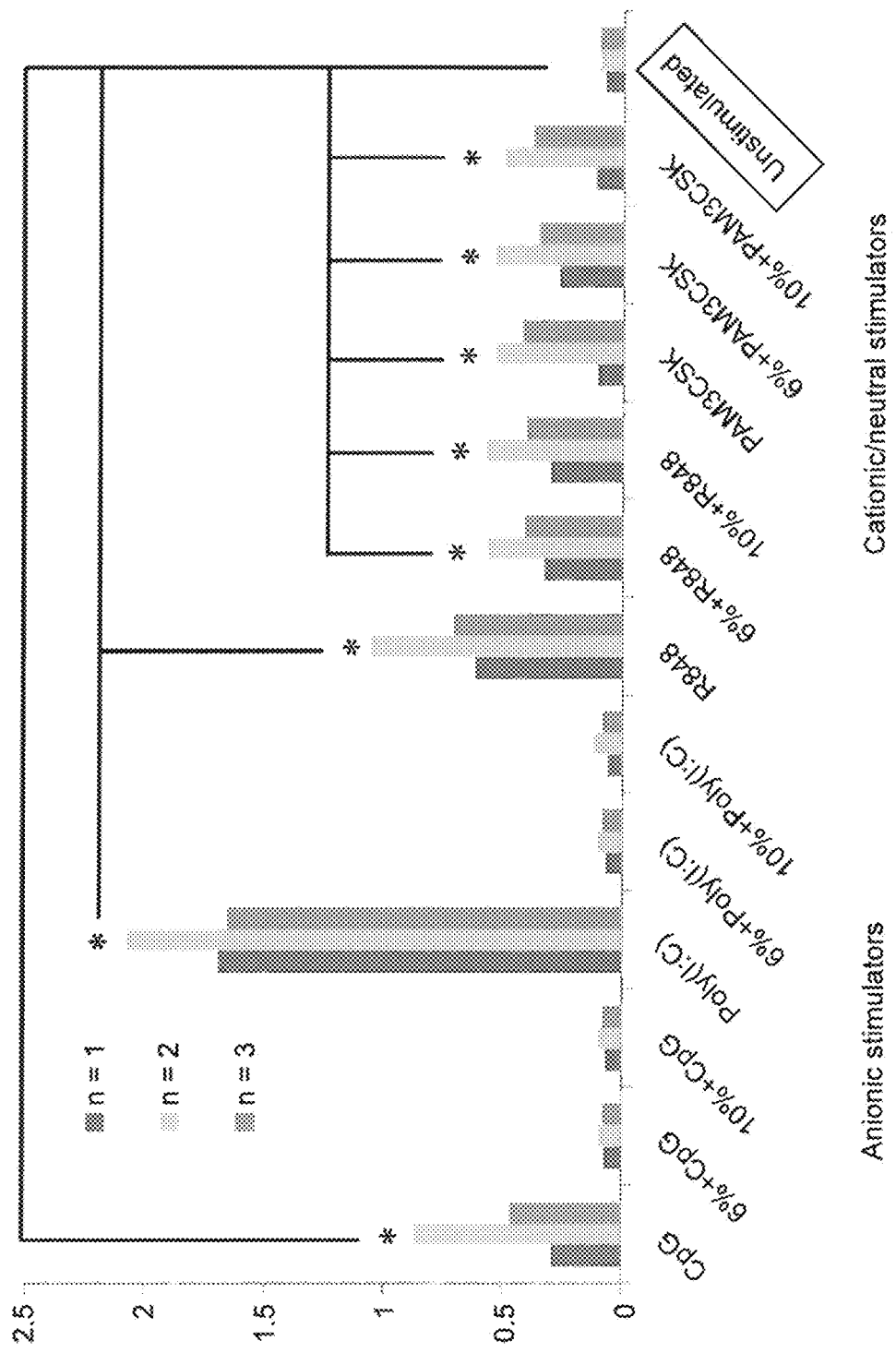
FIG. 8 is a graph comparing the NF-κB expression following TLR activation of cells after incubation with the indicated stimulators and with or without the indicated nanofibers. 6% nanofibers are made with 60% (w/v) neutral polymer and 10% nanofibers are made with 100% (w/v) neutral polymer.

The ability of the polycationic nanofibers to block activation of NF-kB was further tested by incubating B cells with the polycationic nanofibers in the presence of CpG, poly I:C (TLR3) or non-nucleic acid, cationic TLR agonists (R848, PAM3CSK4; structures shown in FIG. 9) at 1 µM for 20 hours. FIG. 8 shows that the polycationic nanofibers selectively inhibit the activity of the nucleic acid (NA) based agonists, CpG and Poly(I:C).

Figure 9:
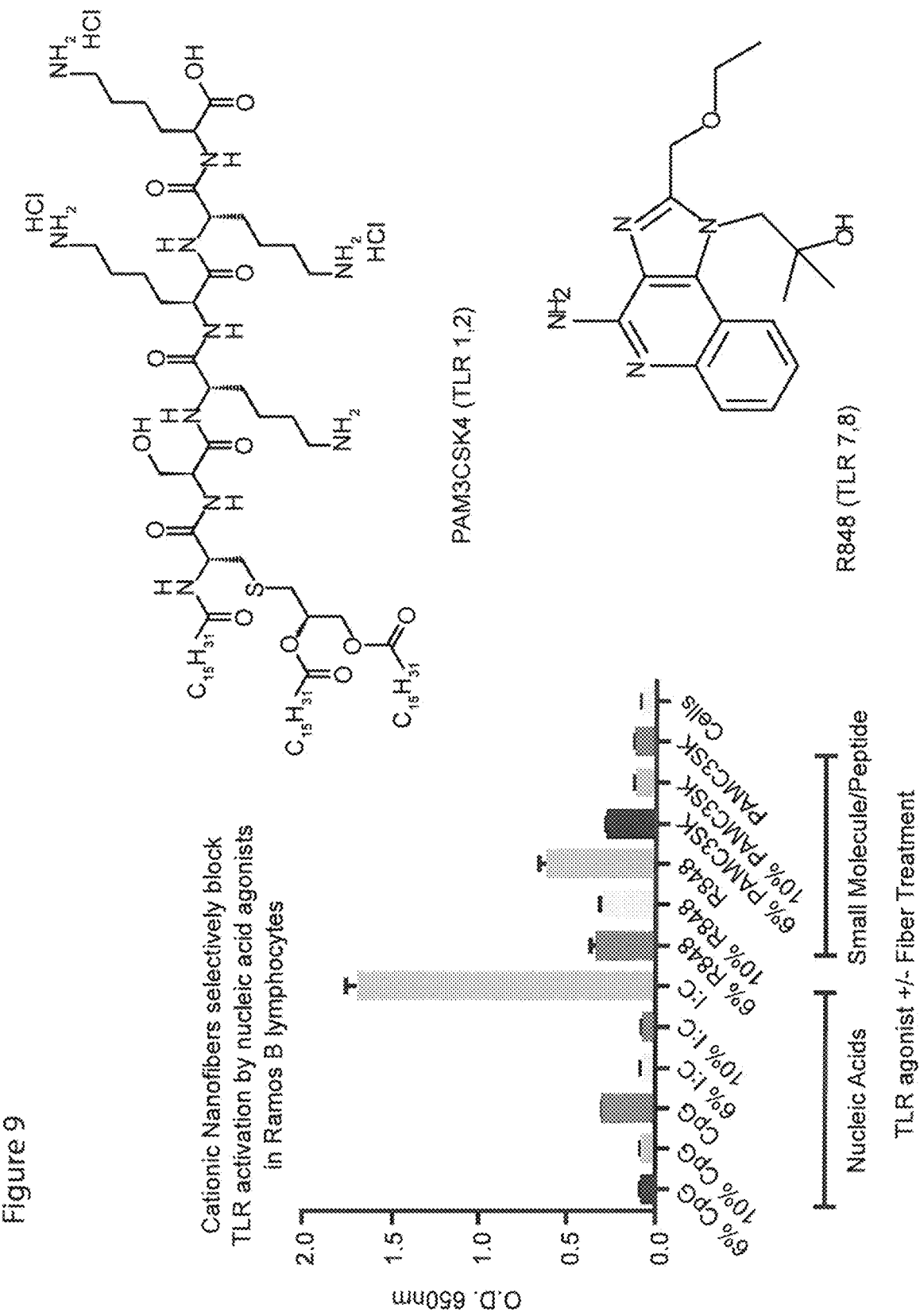
FIG. 9 is a set of drawings showing the structure of the stimulators used and a graph comparing the NF-κB activation in cells after incubation with the indicated stimulators and either no nanofibers or the indicated nanofibers. 6% nanofibers are made with 60% (w/v) neutral polymer and 10% nanofibers are made with 100% (w/v) neutral polymer.

FIG. 9 shows that similar results are obtained to those shown in FIG. 8 when the polycationic nanofibers are pre-incubated with the media containing the TLR agonists prior to the media being added to the Ramos Blue cells for 20 hours and subsequent measurement of alkaline phosphatase production as a read out of NF-κB induction. Thus the TLR agonists are likely absorbed by the polycationic nanofibers and pulled out of the media or solution.

Figure 10:
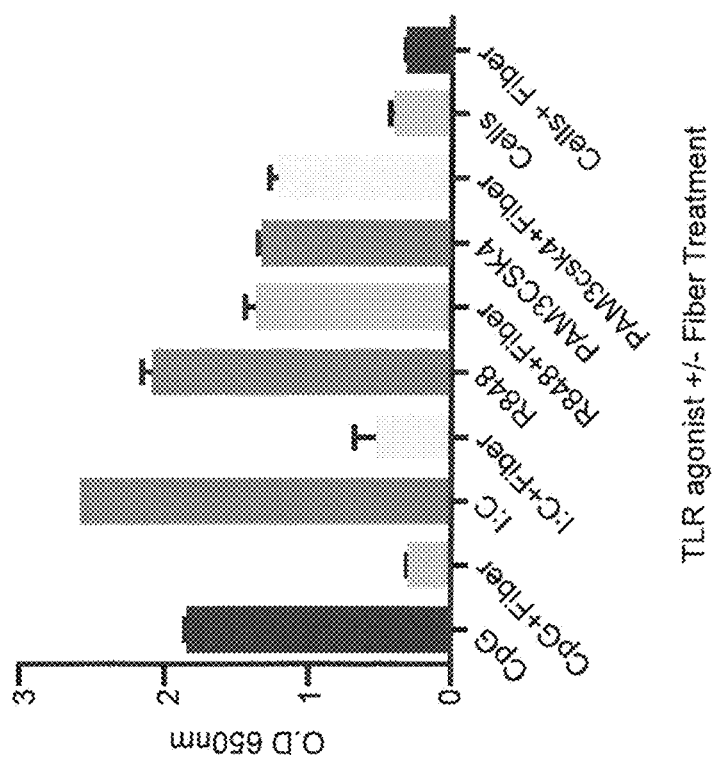
FIG. 10 is a graph showing the NF-κB expression in cells co-incubated with the indicated stimulators and polycationic nanofibers for 4 hours, followed by removal of the polycationic nanofibers; NF-κB expression was determined 16 hrs after polycationic nanofiber removal. The data demonstrate the polycationic nanofibers were able to scavenge and remove the nucleic acid stimulators and prevent NF-κB induction in the presence of cells.

FIG. 10 shows that the polycationic nanofibers can be incubated with the TLR agonist and the cells for as little as 4 hours, and result in a lack of NF-κB activation by nucleic acid agonists. In these experiments the cells were incubated with the nucleic acid agonists and the polycationic nanofibers for 4 hours and then the nanofibers were removed prior to addition of the B cells. After 16 hours continued incubation, alkaline phosphatase levels indicated a lack of activation in the presence of the polycationic nanofibers for CpG and poly I:C, but no effect on PAMcsk4. The nanofibers appear to have scavenged the nucleic acid agonists and removed the agonists from the media when the fibers were pre-incubated in the media+agonists before being exposed to cells as well as when the fibers were incubated with the cells in the presence of agonists.

Figure 11:
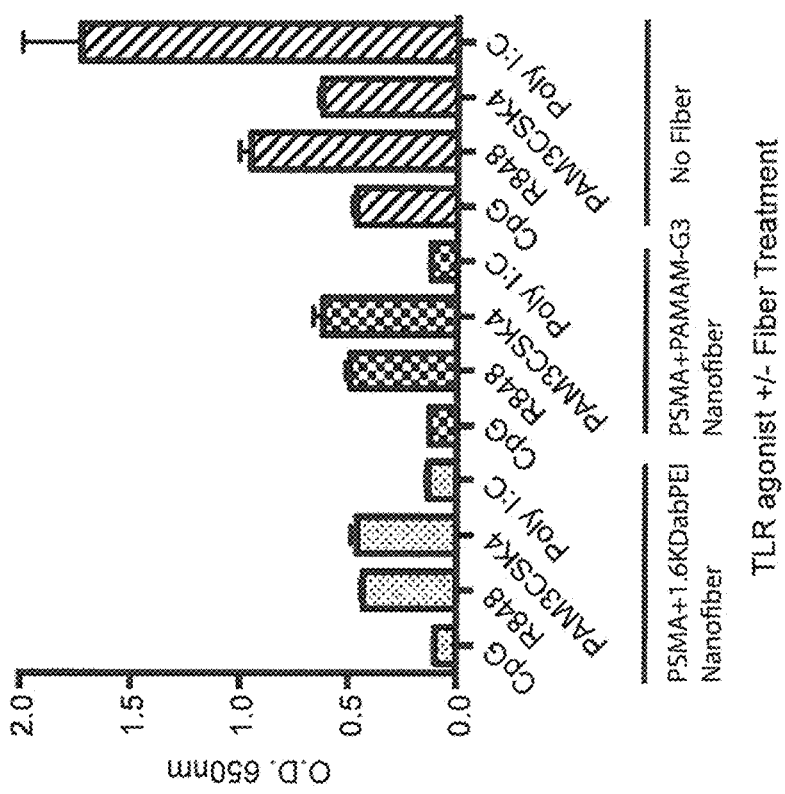
FIG. 11 is a graph showing that similar results were obtained using PAMAM as the cationic polymer and in the presence of serum.
Figure 12:
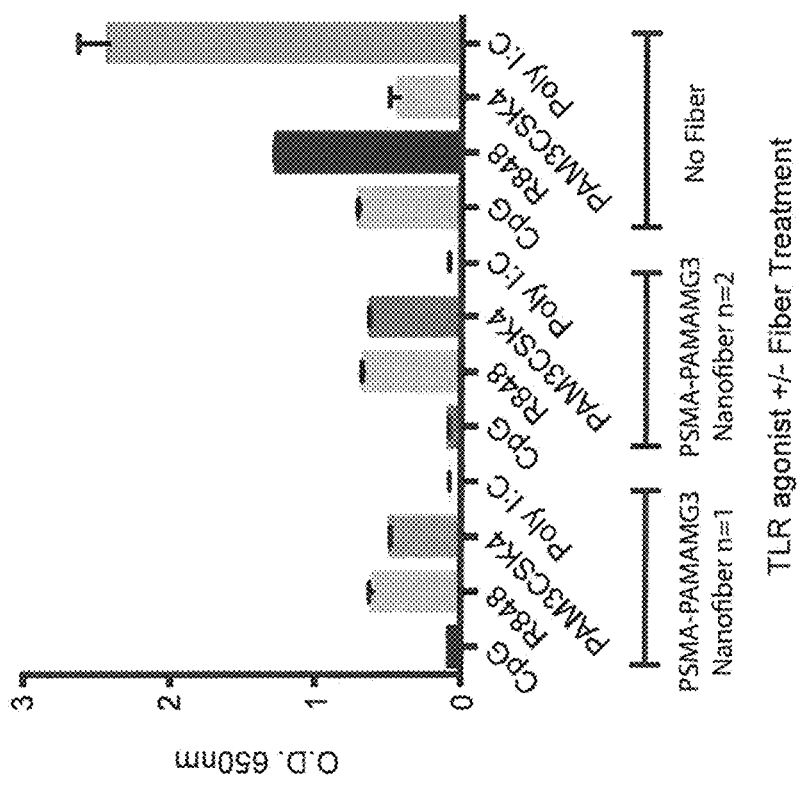
FIG. 12 is a graph showing that similar results were obtained using PAMAM as the cationic polymer and in the presence of serum.

FIG. 11 demonstrates that the polycationic nanofibers are still capable of scavenging the nucleic acid agonists in the presence of serum and activation of NF-κB was blocked. FIG. 12 shows that similar results were obtained with a polycationic nanofiber made with PAMAM instead of bPEI as the cationic polymer.

Figure 13:
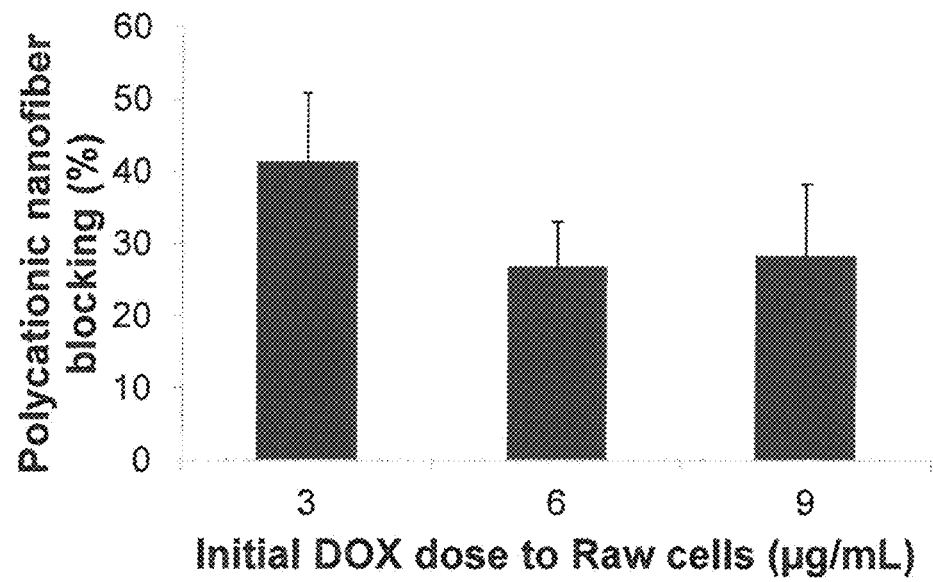
FIG. 13 is a graph showing the ability of the polycationic nanofibers to block secreted alkaline phosphatase production from Ramos-blue cells which contain a NF-κB-alkaline phosphatase reporter construct. Initial DOX dose to Raw cells describes the amount of DOX used to treat Raw cells 48 hrs prior to using the Raw cell debris for activation of the Ramos-blue cells. Polycationic nanofiber blocking demonstrates the polycationic nanofiber's ability to prevent NF-κB production by scavenging immune-stimulating cell debris from the media.

FIG. 13 demonstrates a biological application of the polycationic nanofibers in the form of reducing chemotherapeutic toxicity; the polycationic nanofiber reduces the subsequent NF-κβ expression in Ramos-Blue cells by as much as 40%. Given that the Ramos-Blue cells release NF-κβ due to activation by various agonists, not limited to nucleic acids, it is reasonable to assume that the polycationic nanofibers are able to scavenge out a significant amount of extracellular nucleic acids released from DOX-killed RAW cells.

Figure 15:
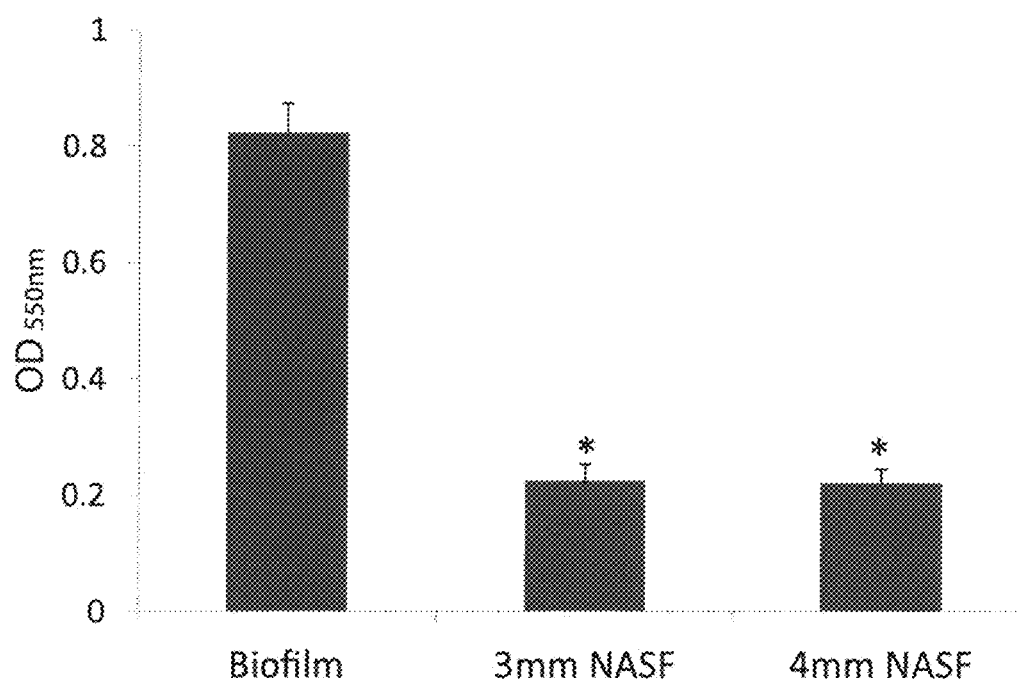
FIG. 15 is a graph showing polycationic nanofibers prevent *Pseudomonas aeruginosa* biofilm formation after 48 hrs. 3 mm and 4 mm indicate the diameter of the circular polycationic nanofiber mesh used in the experiment.
Figure 14B:
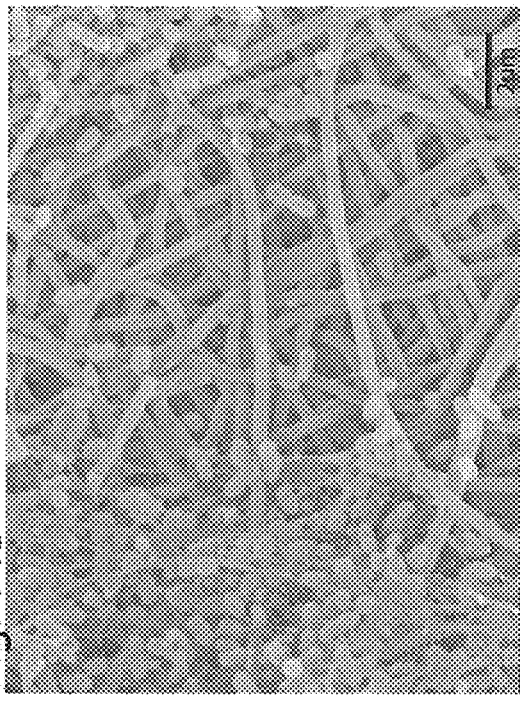
FIG. 14A-14D show a set of scanning electron micrograph photographs showing the polycationic nanofibers and their interaction with *Pseudomonas aeruginosa*.
Figure 14D:
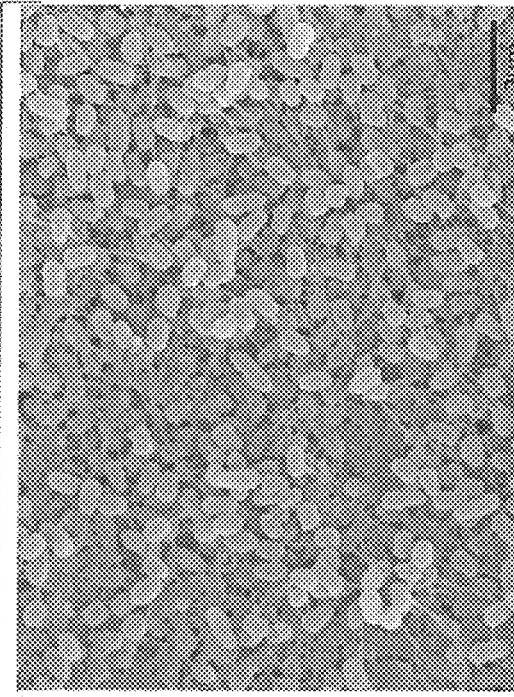
Figure 14A:
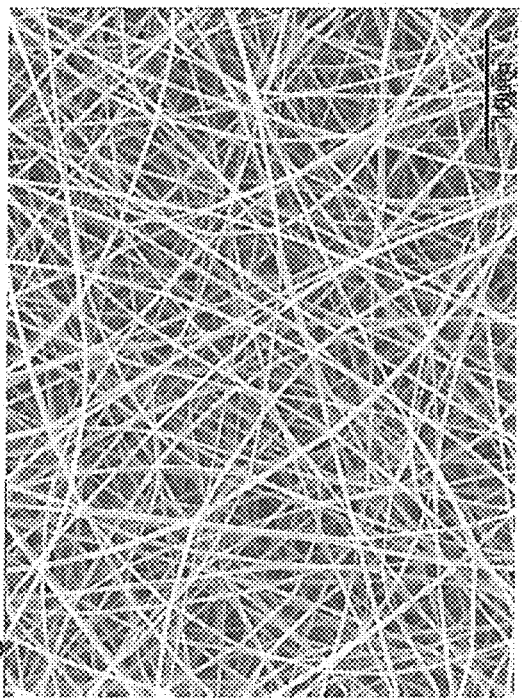
Figure 14C:
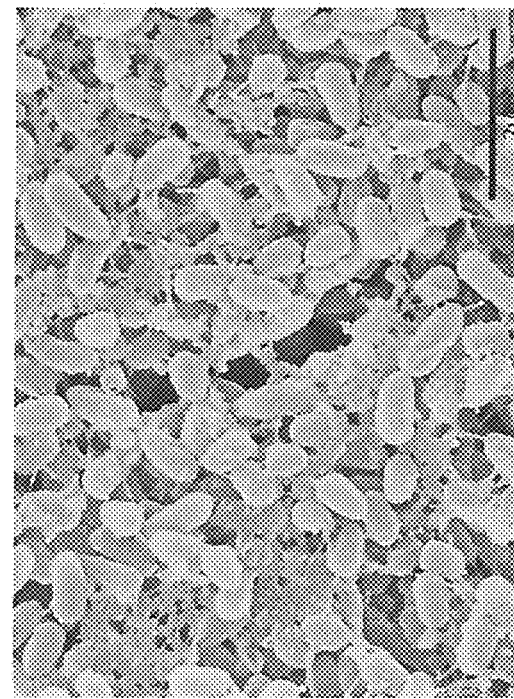
Figure 16B:
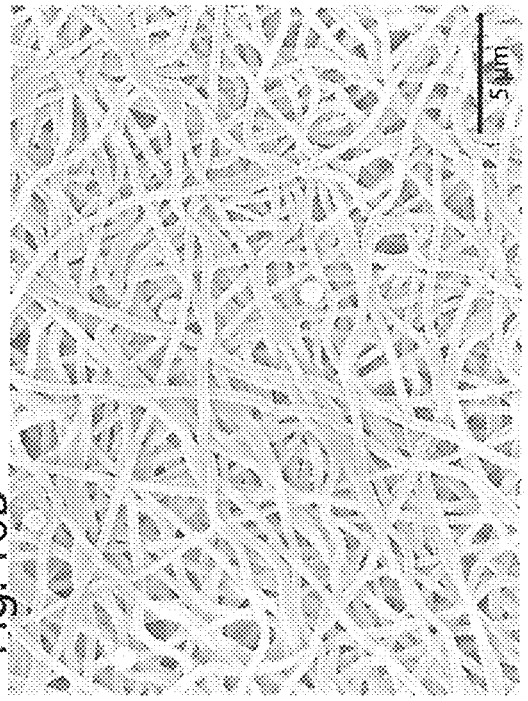
FIG. 16A-16D show a set of SEM images showing polycationic nanofibers and their intercation with *Staphylococcus aureus*.
Figure 16D:
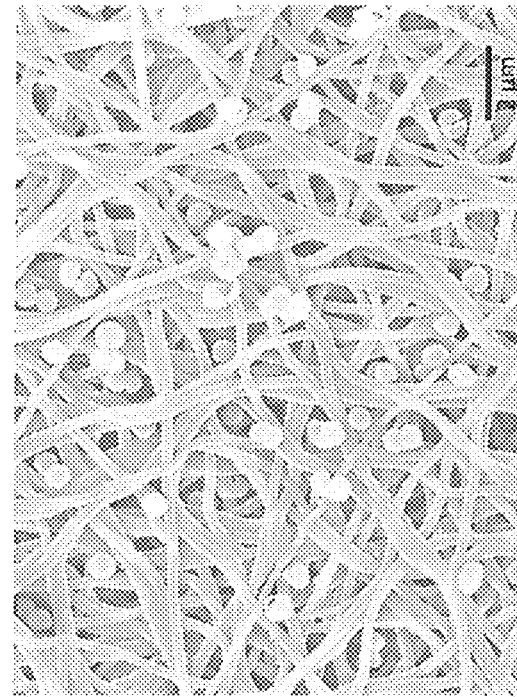
Figure 16A:
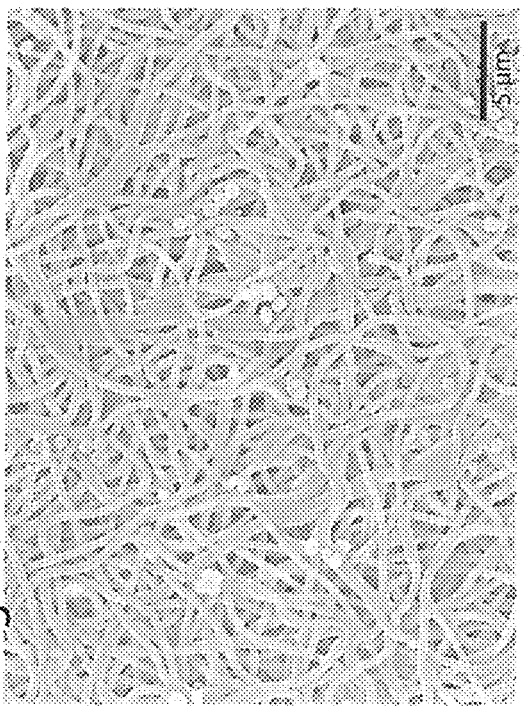
Figure 16C:
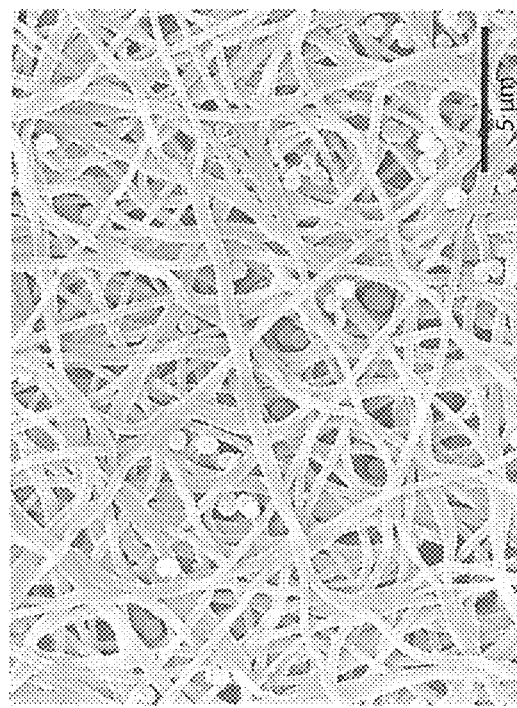
Figure 17:
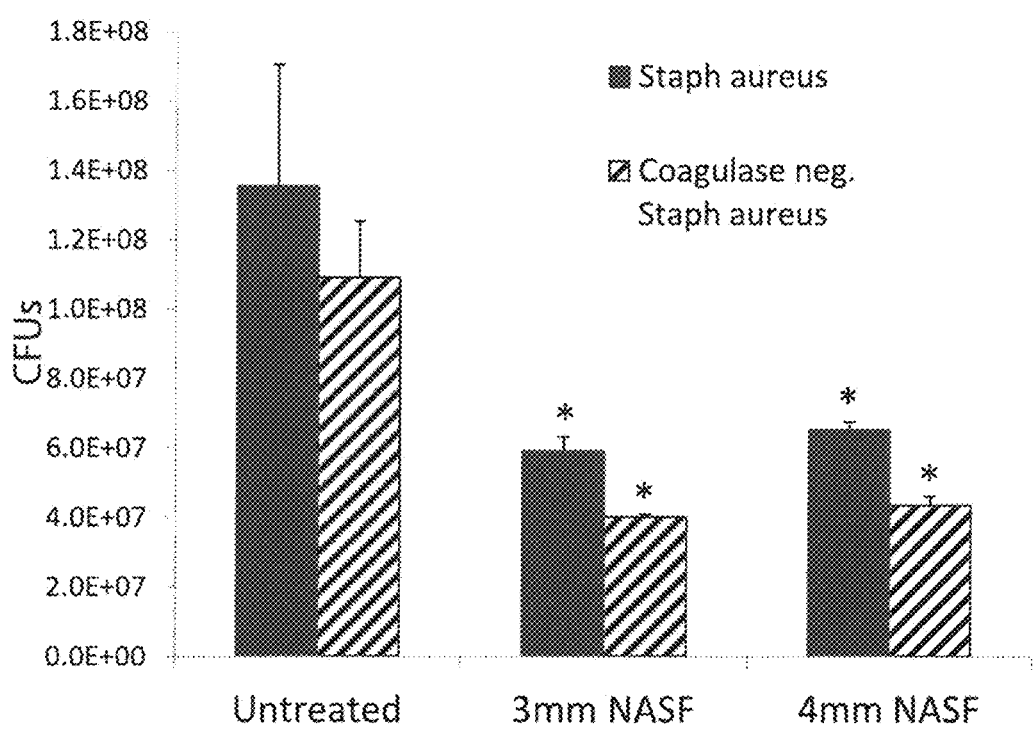
FIG. 17 is a graph showing the effect of polycationic nanofibers on *S. aureus* and coagulase negative *S. aureus* bacterial cell growth as represented by Colony Forming Units (CFUs). The * represent statistical significance of $p<0.05$ as compared to untreated.

FIG. 14A-14D show SEM images of *Pseudomonas aeruginosa* biofilm formation on the surface of the polycationic nanofibers after 24 hrs (FIG. 14B) and 48 hrs (FIG. 14C,D) as compared to the original electrospun nanofiber (FIG. 14A). FIG. 15 shows that treatment with polycationic nanofibers significantly reduces the total biofilm mass on an adjacent surface. FIG. 16A-16D shows SEM images of polycationic nanofibers after 48 hrs incubation with (FIG. 16A-B) *Staphylococcus aureus* and (FIG. 16C-D) Coagulase-negative *Staphylococcus aureus*. The images suggest that the polycationic nanofibers do not promote biofilm growth of these two types of *Staphylococcus aureus*. FIG. 15 shows that the polycationic nanofibers reduce the total number of bacterial CFUs after 48 hrs of incubation therefore demonstrating their utility in reducing infection and potentially preventing biofilm formation.

We claim:

1. A method of using a polycationic nanofiber comprising administering the polycationic nanofibers to a subject in an amount effective to adsorb anionic compounds in the subject,
   wherein the anionic compounds are pro-inflammatory or immunostimulatory anionic molecules or anionic anticoagulant polymers and
   wherein the polycationic nanofiber is prepared by a method comprising (a) electrospinning a neutral polymer to produce nanofibers less than 2 µm in diameter and (b) grafting a cationic polymer onto the neutral polymer nanofibers to produce the polycationic nanofiber.

2. The method of claim 1, wherein the administration and absorption is effective to reduce inflammation.

3. The method of claim 1, wherein the polycationic nanofibers are administered in an amount effective to inhibit nucleic acid-induced activation of PRRs.

4. The method of claim 1, wherein the polycationic nanofibers are administered in an amount effective to inhibit formation of a biofilm or inhibit growth of a microbe capable of forming a biofilm or infectious wound.

5. The method of claim 4, wherein the biofilm comprises bacteria or fungi.

6. The method of claim 5, wherein the bacteria are selected from the group consisting of *Bacillus* spp., *Corynebacterium* spp., *Listeria* spp. (i.e. *Listeria monocytogenes*), *Staphylococcus* spp. (i.e. *Staphylococcus aureus* and *Staphylococcus epidermis*), *Micrococcus* spp., and lactic acid bacteria (i.e. *Lactobacillus plantarum, Lactococcus lactis, Entercoccus* spp., *Streptococcus* spp. including *Streptococcus mutans* and *Streptococcus pneumoniae*).

7. The method of claim 5, wherein the bacteria are selected from the group consisting of *Escherichia* spp. (i.e. *Escherichia coli*), *Klebsiella* spp. (i.e. *Klebsiella pneumonia*), *Pseudomonas* spp. (i.e. *Pseudomonas aeruginosa, Pseudomonas putida, Pseudomonas fluorescens*), *Proteus* spp., *Legionella* spp., *Rhizobium* spp. (i.e. *Rhizobium leguminosarum*), *Sinorhizobium* spp. (i.e. *Sinorhizobium meliloti*), and *Serratia* spp.

8. The method of claim 5, wherein the fungi are selected from the group consisting of *Candida* and *Aspergillus*.

9. The method of claim 1, wherein the polycationic nanofibers are incorporated into a medical device, filter, dressing, graft, or mesh.

10. The method of claim 1, wherein the subject has an inflammatory disease or condition, an autoimmune disease, a chronic wound or has been treated with an anticoagulant.

11. The method of claim 1, wherein the anionic compounds are pro-inflammatory or immunostimulatory anionic molecules.

12. The method of claim 1, wherein the anionic compounds are anionic anticoagulant polymers.

13. The method of claim 1, wherein the neutral polymer is poly-styrene maleic anhydride.

14. The method of claim 1, wherein the cationic polymer is selected from the group consisting of polyethyleneimine (PEI), branched PEI (bPEI), polyamidoamine (PAMAM), in particular PAMAM generations 0-4 or other dendrimers, copolymers containing any combination of N,N'-cystaminebisacrylamide and N,N'-hexamethalyne bisacrylamide backbone components with histamine and 3-(dimethylamino)-1-propylamine linkers.

15. The method of claim 1, wherein the nanofibers are between 0.1 μm and 2 μm in diameter.

* * * * *